US010363032B2

(12) United States Patent
Scheib et al.

(10) Patent No.: US 10,363,032 B2
(45) Date of Patent: Jul. 30, 2019

(54) SURGICAL STAPLER WITH HYDRAULIC DECK CONTROL

(71) Applicant: Ethicon Endo-Surgery, LLC, Guaynabo, PR (US)

(72) Inventors: Charles J. Scheib, Loveland, OH (US); Michael J. Vendely, Lebanon, OH (US); Jason L. Harris, Lebanon, OH (US)

(73) Assignee: Ethicon LLC, Guaynabo, PR (US)

( * ) Notice: Subject to any disclaimer, the term of this patent is extended or adjusted under 35 U.S.C. 154(b) by 422 days.

(21) Appl. No.: 15/133,381

(22) Filed: Apr. 20, 2016

(65) Prior Publication Data

US 2017/0303925 A1     Oct. 26, 2017

(51) Int. Cl.
*A61B 17/072* (2006.01)
*A61B 17/068* (2006.01)
(Continued)

(52) U.S. Cl.
CPC .......... *A61B 17/068* (2013.01); *A61B 17/072* (2013.01); *A61B 17/105* (2013.01);
(Continued)

(58) Field of Classification Search
CPC .......... A61B 2017/07242; A61B 2017/07271; A61B 2017/07278; A61B 2017/0725;
(Continued)

(56) References Cited

U.S. PATENT DOCUMENTS

| 4,805,823 A | 2/1989 | Rothfuss |
| 5,219,111 A * | 6/1993 | Bilotti .................. A61B 17/072 227/175.1 |

(Continued)

FOREIGN PATENT DOCUMENTS

| EP | 1 785 097 A2 | 5/2007 |
| EP | 1 884 201 A1 | 2/2008 |
| WO | WO 2016044216 A1 * | 3/2016 ....... A61B 17/07207 |

OTHER PUBLICATIONS

European Search Report and Written Opinion dated Jul. 10, 2017 for Application No. EP 17167069.8, 12 pgs.

(Continued)

*Primary Examiner* — Stephen F. Gerrity
*Assistant Examiner* — Joshua G Kotis
(74) *Attorney, Agent, or Firm* — Frost Brown Todd LLC

(57) ABSTRACT

A surgical instrument includes a body, a shaft assembly, and an end effector. The end effector a first jaw, a second jaw, and a staple cartridge. The first jaw has an anvil that is configured to form a plurality of staples. The first jaw is movable relative to the second jaw from an open configuration toward a closed configuration for capturing the tissue therebetween and forming the staples therein. The staple cartridge includes a plurality of staples, a body, and a deck. The body is received by the second jaw. The deck has a plurality of staple pockets such that the plurality of staples are configured to pass through staple pockets. The deck is configured to selectively move relative to the body from a first position to a second position for adjusting a height of the deck relative to the anvil while the body is received in the second jaw.

20 Claims, 16 Drawing Sheets

(51) Int. Cl.
 *A61B 17/10* (2006.01)
 *A61B 17/00* (2006.01)
(52) U.S. Cl.
 CPC .............. *A61B 2017/00539* (2013.01); *A61B 2017/0725* (2013.01); *A61B 2017/07242* (2013.01); *A61B 2017/07271* (2013.01); *A61B 2017/07278* (2013.01)
(58) Field of Classification Search
 CPC .......... A61B 2017/00535; A61B 2017/00539; A61B 2017/00544
 See application file for complete search history.

(56) References Cited

U.S. PATENT DOCUMENTS

| | | | |
|---|---|---|---|
| 5,415,334 A | 5/1995 | Williamson et al. | |
| 5,465,895 A | 11/1995 | Knodel et al. | |
| 5,533,521 A * | 7/1996 | Granger | A61B 90/06 600/587 |
| 5,597,107 A | 1/1997 | Knodel et al. | |
| 5,632,432 A | 5/1997 | Schulze et al. | |
| 5,673,840 A | 10/1997 | Schulze et al. | |
| 5,704,534 A | 1/1998 | Huitema et al. | |
| 5,792,135 A | 8/1998 | Madhani et al. | |
| 5,814,055 A | 9/1998 | Knodel et al. | |
| 5,817,084 A | 10/1998 | Jensen | |
| 5,878,193 A | 3/1999 | Wang et al. | |
| 5,919,198 A * | 7/1999 | Graves, Jr. | A61B 17/07207 227/176.1 |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 6,978,921 B2 | 12/2005 | Shelton et al. | |
| 7,000,818 B2 | 2/2006 | Shelton et al. | |
| 7,143,923 B2 | 12/2006 | Shelton et al. | |
| 7,303,108 B2 | 12/2007 | Shelton | |
| 7,367,485 B2 | 5/2008 | Shelton et al. | |
| 7,380,695 B2 | 6/2008 | Doll et al. | |
| 7,380,696 B2 | 6/2008 | Shelton et al. | |
| 7,404,508 B2 | 7/2008 | Smith et al. | |
| 7,434,715 B2 | 10/2008 | Shelton et al. | |
| 7,472,815 B2 | 1/2009 | Shelton, IV et al. | |
| 7,524,320 B2 | 4/2009 | Tierney et al. | |
| 7,691,098 B2 | 4/2010 | Wallace et al. | |
| 7,721,930 B2 | 5/2010 | McKenna et al. | |
| 7,806,891 B2 | 10/2010 | Nowlin et al. | |
| 8,141,762 B2 | 3/2012 | Bedi et al. | |
| 8,210,411 B2 | 7/2012 | Yates et al. | |
| 8,371,491 B2 | 2/2013 | Huitema et al. | |
| 8,408,439 B2 | 4/2013 | Huang et al. | |
| 8,453,914 B2 | 6/2013 | Laurent et al. | |
| 8,479,969 B2 | 7/2013 | Shelton | |
| 8,573,461 B2 | 11/2013 | Shelton et al. | |
| 8,573,465 B2 | 11/2013 | Shelton | |
| 8,602,288 B2 | 12/2013 | Shelton | |
| 8,616,431 B2 | 12/2013 | Timm et al. | |
| 8,783,541 B2 | 7/2014 | Shelton et al. | |
| 8,800,838 B2 | 8/2014 | Shelton | |
| 8,820,605 B2 | 9/2014 | Shelton | |
| 8,844,789 B2 | 9/2014 | Shelton et al. | |
| 8,955,732 B2 | 2/2015 | Zemlok et al. | |
| 9,186,142 B2 | 11/2015 | Fanelli et al. | |
| 9,301,759 B2 | 4/2016 | Spivey et al. | |
| 2007/0073340 A1 * | 3/2007 | Shelton, IV | A61B 17/07207 606/219 |
| 2007/0102473 A1 * | 5/2007 | Shelton, IV | A61B 17/07207 227/175.1 |
| 2007/0125826 A1 * | 6/2007 | Shelton, IV | A61B 17/07207 227/175.1 |
| 2011/0006101 A1 * | 1/2011 | Hall | A61B 90/30 227/175.2 |
| 2012/0193396 A1 * | 8/2012 | Zemlok | A61B 17/07207 227/177.1 |
| 2012/0241491 A1 * | 9/2012 | Aldridge | A61B 17/07292 227/175.1 |
| 2012/0241493 A1 * | 9/2012 | Baxter, III | A61B 17/07292 227/175.1 |
| 2012/0318844 A1 * | 12/2012 | Shelton, IV | A61B 90/92 227/176.1 |
| 2014/0239036 A1 | 8/2014 | Zerkle et al. | |
| 2014/0239037 A1 | 8/2014 | Boudreaux et al. | |
| 2014/0239038 A1 | 8/2014 | Leimbach et al. | |
| 2014/0239040 A1 | 8/2014 | Fanelli et al. | |
| 2014/0239041 A1 | 8/2014 | Zerkle et al. | |
| 2014/0239042 A1 | 8/2014 | Simms et al. | |
| 2014/0239043 A1 | 8/2014 | Simms et al. | |
| 2014/0239044 A1 | 8/2014 | Hoffman | |
| 2015/0272575 A1 | 10/2015 | Leimbach et al. | |
| 2015/0297225 A1 * | 10/2015 | Huitema | A61B 17/068 227/176.1 |
| 2015/0374360 A1 | 12/2015 | Scheib et al. | |
| 2015/0374361 A1 | 12/2015 | Gettinger et al. | |
| 2017/0303924 A1 * | 10/2017 | Scheib | A61B 17/068 |

OTHER PUBLICATIONS

International Search Report and Written Opinion dated Jul. 13, 2017 for Application No. PCT/US2017/027950, 17 pgs.

* cited by examiner

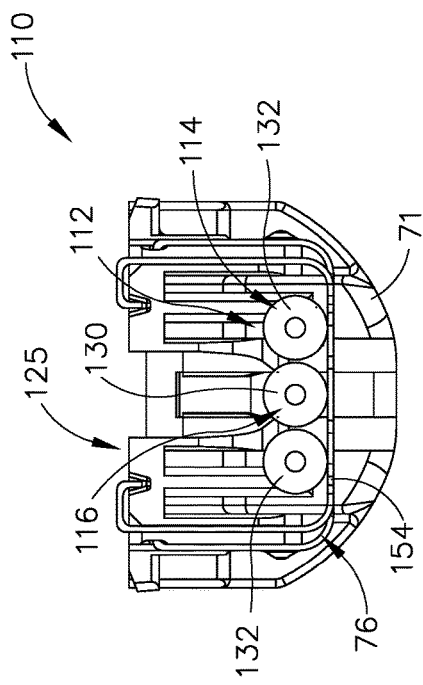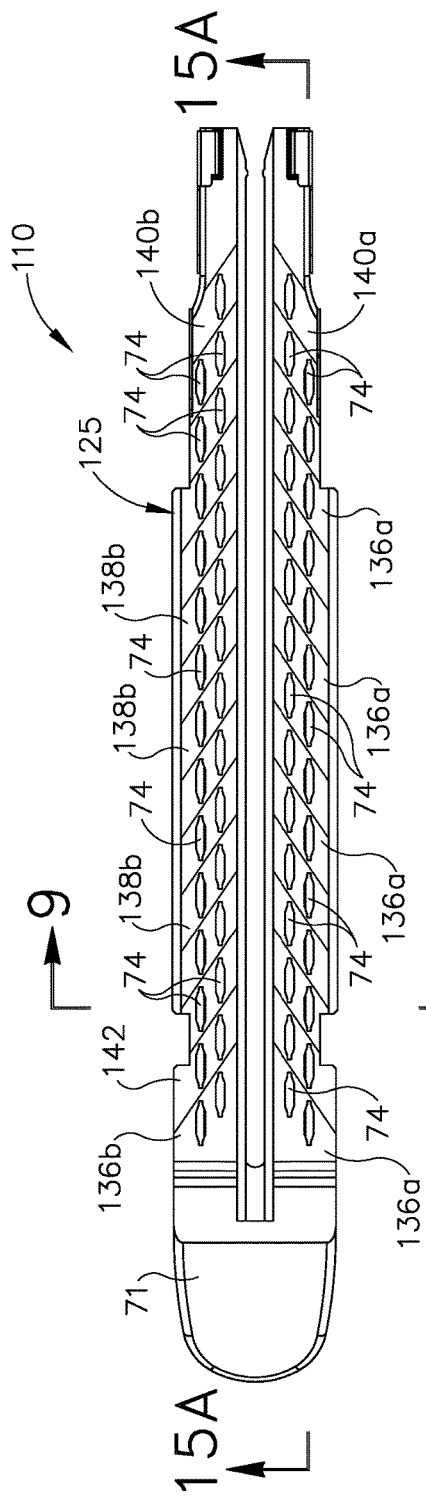
Fig.7
Fig.8

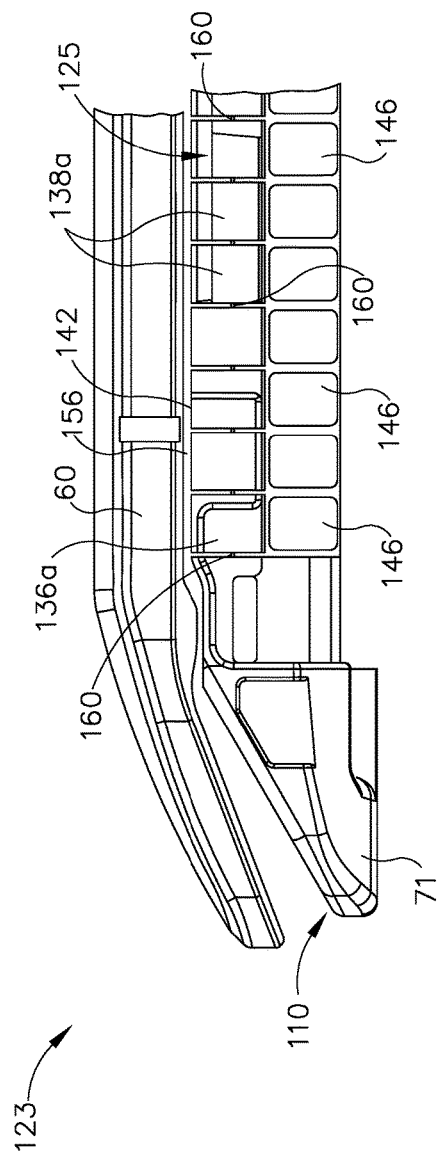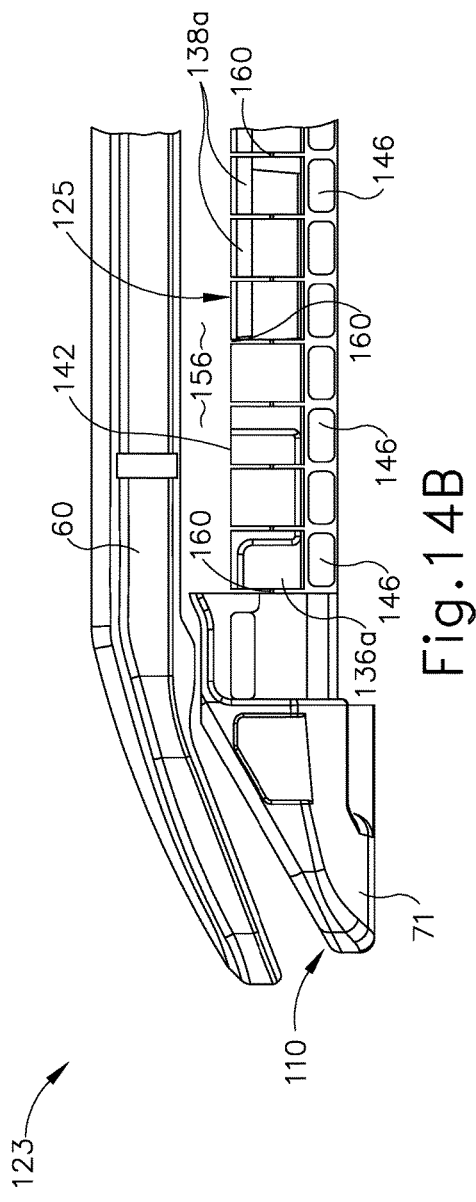

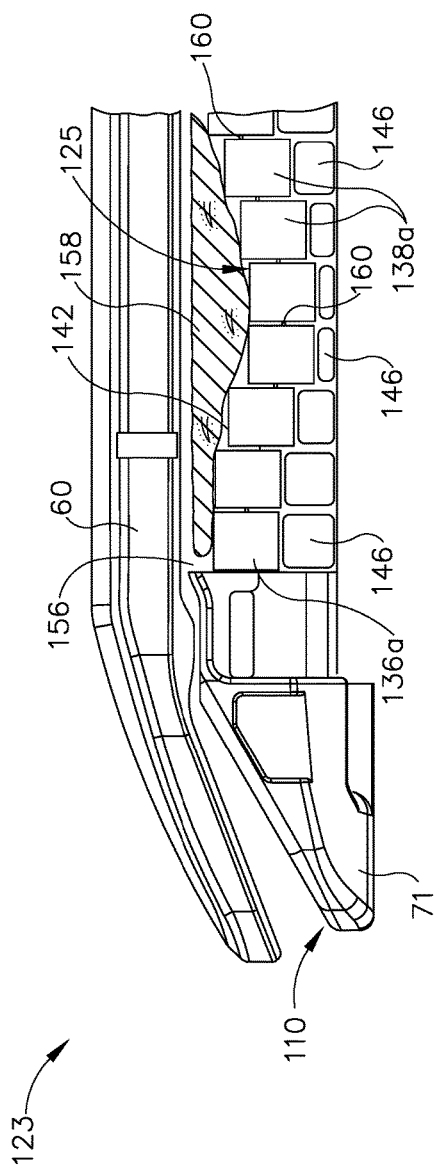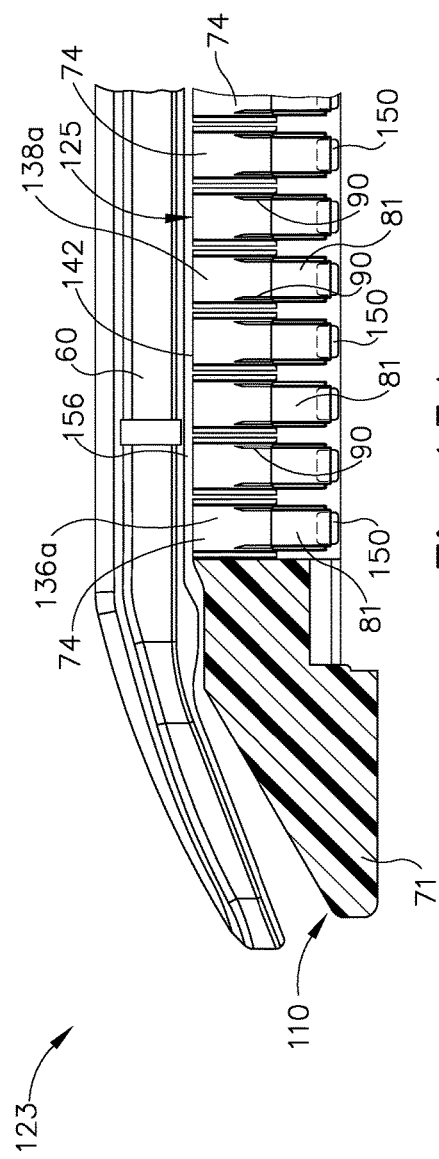

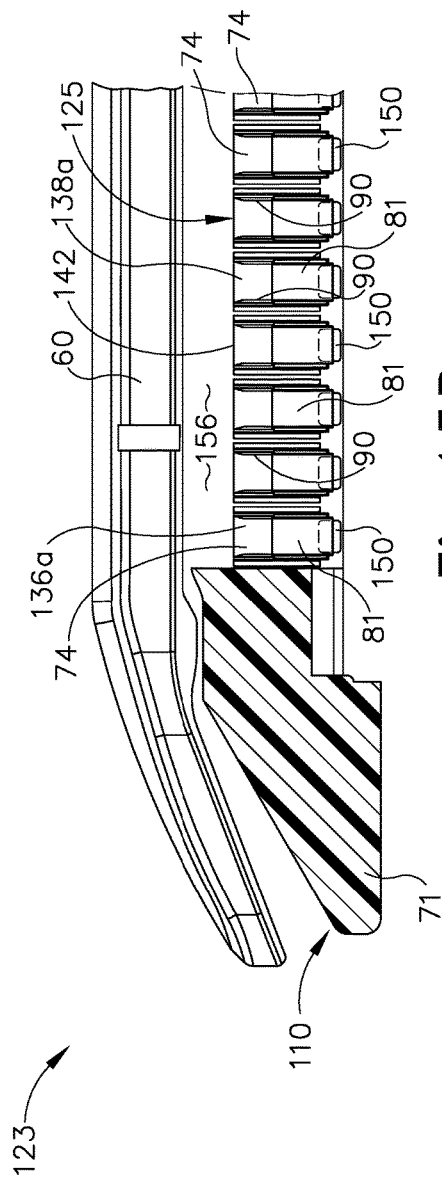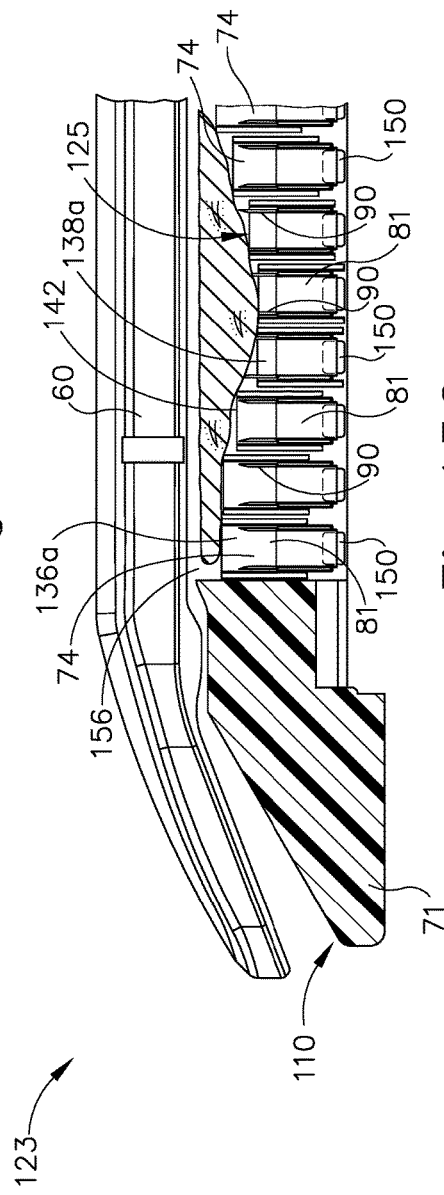

SURGICAL STAPLER WITH HYDRAULIC DECK CONTROL

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432,entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited for use through a thoracotomy are disclosed in U.S. Patent Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015; U.S. Patent Pub. No. 2014/0239041, entitled "Lockout Feature for Movable Cutting Member of Surgical Instrument," published Aug. 28, 2014, issued as U.S. Pat. No. 9,717,497 on Aug. 1, 2017; U.S. Patent Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; U.S. Patent Pub. No. 2014/0239036, entitled "Jaw Closure Feature for End Effector of Surgical Instrument," published Aug. 28, 2014, issued as U.S. Pat. No. 9,839,421 on Dec. 12, 2017; U.S. Patent Pub. No. 2014/0239040, entitled "Surgical Instrument with Articulation Lock having a Detenting Binary Spring," published Aug. 28, 2014, issued as U.S. Pat. No. 9,867,615 on Jan. 16, 2018; U.S. Patent Pub. No. 2014/0239043, entitled "Distal Tip Features for End Effector of Surgical Instrument," published Aug. 28, 2014, issued as U.S. Pat. No. 9,622,746 on Apr. 18, 2017; U.S. Patent Pub. No. 2014/0239037, entitled "Staple Forming Features for Surgical Stapling Instrument," published Aug. 28, 2014, issued as U.S. Pat. No. 10,092,292 on Oct. 9, 2018; U.S. Patent Pub. No. 2014/0239038, entitled "Surgical Instrument with Multi-Diameter Shaft," published Aug. 28, 2014, issued as U.S. Pat. No. 9,795,379 on Oct. 24, 2017; and U.S. Patent Pub. No. 2014/0239044, entitled "Installation Features for Surgical Instrument End Effector Cartridge," published Aug. 28, 2014, issued as U.S. Pat. No. 9,808,248 on Nov. 7, 2017. The disclosure of each of the above-cited U.S. Patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 7 depicts a rear end view of the staple cartridge of FIG. 5;

FIG. 8 depicts a top plan view of the staple cartridge of FIG. 5;

FIG. 14A depicts an enlarged cross-sectional side view of the distal end of the end effector of FIG. 5, with various components removed for clarity, and with the deck in an upper position;

FIG. 14B depicts an enlarged cross-sectional side view of the distal end of the end effector of FIG. 5, with various components removed for clarity, and with the deck in a lower position;

FIG. 14C depicts an enlarged cross-sectional side view of the distal end of the end effector of FIG. 5, with various components removed for clarity, and with the deck in a position between the upper and lower positions having received tissue thereagainst;

FIG. 15A depicts an enlarged cross-sectional view of the distal end of the end effector of FIG. 5 taken along section line 15A-15A of FIG. 8, with the deck in the upper position and having various components removed for clarity;

FIG. 15B depicts an enlarged cross-sectional view of the distal end of the end effector of FIG. 5 taken along section line 15A-15A of FIG. 8, with the deck in the lower position;

FIG. 15C depicts an enlarged cross-sectional view of the distal end of the end effector of FIG. 5 taken along section line 15A-15A of FIG. 8, with the deck in a position between the upper and lower positions having received a tissue thereagainst and the hydraulic staple drive system in an unfired state.

Figure 1:
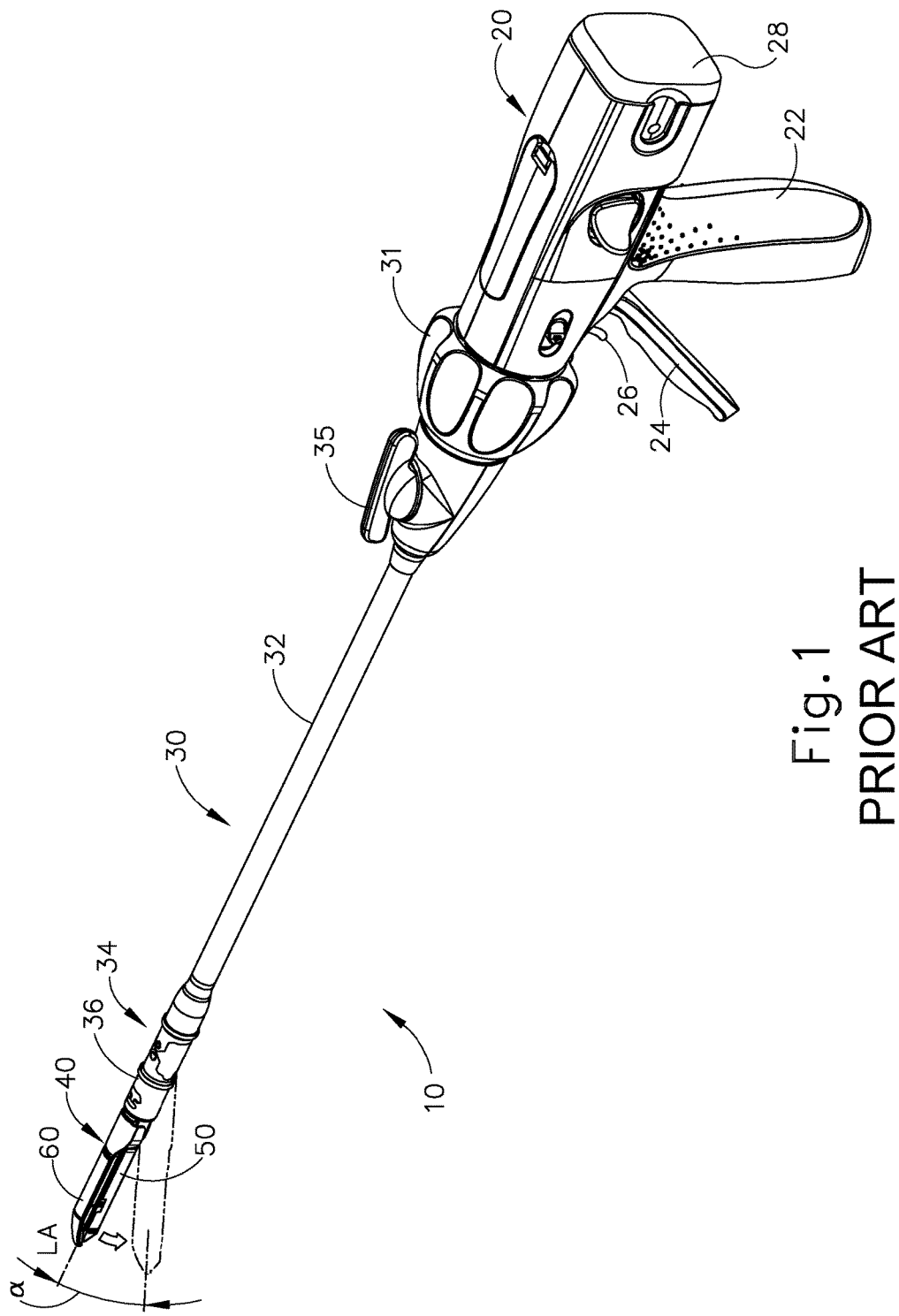
FIG. 1 depicts a perspective view of an exemplary articulating surgical stapling instrument.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Stapler

FIG. 1 depicts an exemplary surgical stapling and severing instrument (10) that includes a handle assembly (20), a shaft assembly (30), and an end effector (40). End effector (40) and the distal portion of shaft assembly (30) are sized for insertion, in a nonarticulated state as depicted in FIG. 1, through a trocar cannula to a surgical site in a patient for performing a surgical procedure. By way of example only, such a trocar may be inserted in a patient's abdomen, between two of the patient's ribs, or elsewhere. In some settings, surgical instrument (10) is used without a trocar. For instance, end effector (40) and the distal portion of shaft assembly (30) may be inserted directly through a thoracotomy or other type of incision. It should be understood that terms such as "proximal" and "distal" are used herein with reference to a clinician gripping handle assembly (20) of surgical instrument (10). Thus, end effector (40) is distal with respect to the more proximal handle assembly (20). It will be further appreciated that for convenience and clarity, spatial terms such as "vertical" and "horizontal" are used herein with respect to the drawings. However, surgical instruments are used in many orientations and positions, and these terms are not intended to be limiting and absolute.

A. Exemplary Handle Assembly and Shaft Assembly

As shown in FIG. 1, handle assembly (20) of the present example comprises pistol grip (22), a closure trigger (24), and a firing trigger (26). Each trigger (24, 26) is selectively pivotable toward and away from pistol grip (22) as will be described in greater detail below. Handle assembly (20) further includes a removable battery pack (28). These components will also be described in greater detail below. Of course, handle assembly (20) may have a variety of other components, features, and operabilities, in addition to or in lieu of any of those noted above. Other suitable configurations for handle assembly (20) will be apparent to those of ordinary skill in the art in view of the teachings herein.

Figure 2:
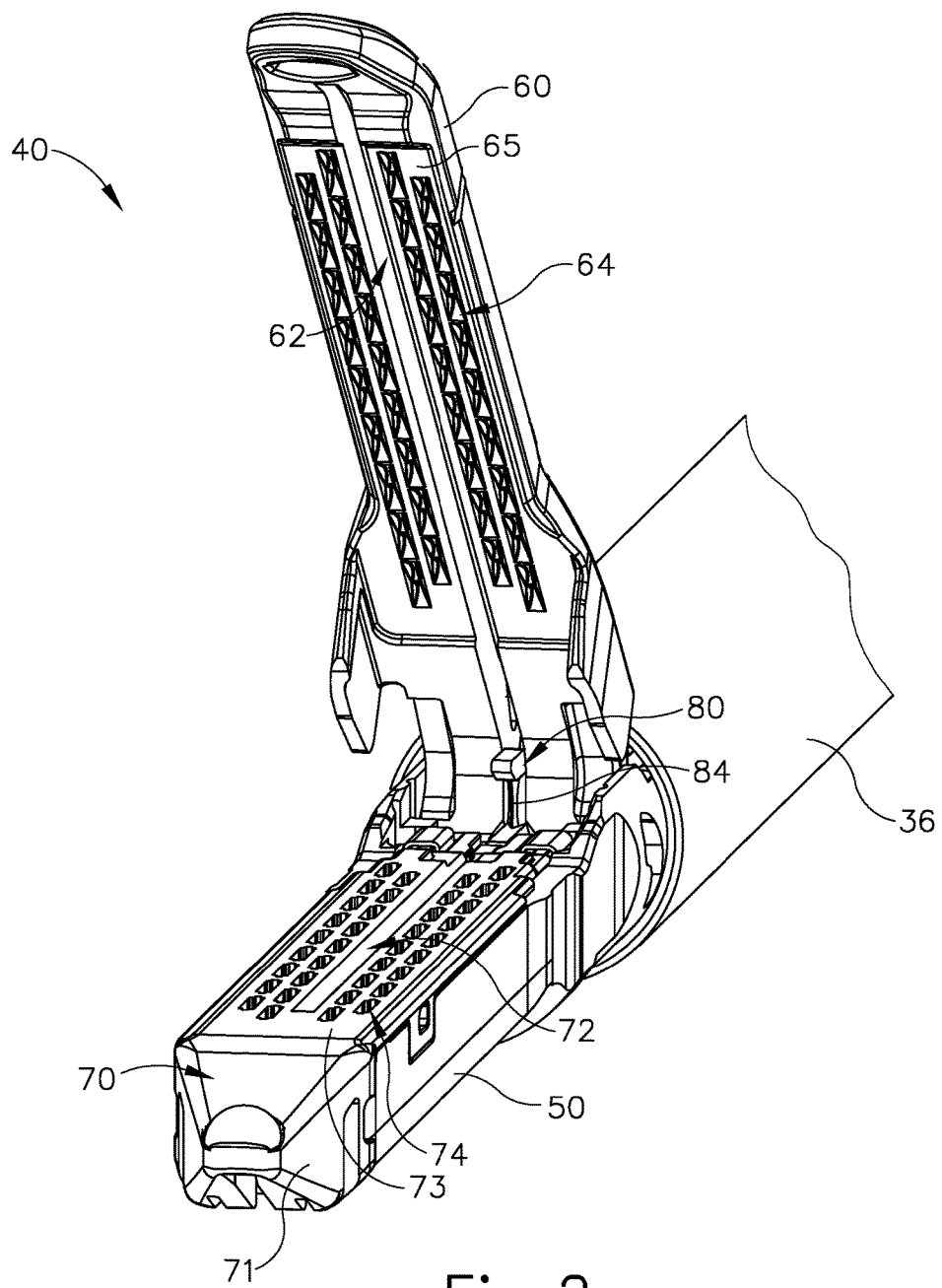
FIG. 2 depicts a perspective view of an end effector of the instrument of FIG. 1, with the end effector in an open configuration showing a first exemplary staple cartridge containing a plurality of staples.

As shown in FIGS. 1-2, shaft assembly (30) of the present example comprises an outer closure tube (32), an articulation section (34), and a closure ring (36), which is further coupled with end effector (40). Closure tube (32) extends along the length of shaft assembly (30). Closure ring (36) is positioned distal to articulation section (34). Closure tube (32) and closure ring (36) are configured to translate longitudinally relative to handle assembly (20). Longitudinal translation of closure tube (32) is communicated to closure ring (36) via articulation section (34).

Articulation section (34) is operable to laterally deflect closure ring (36) and end effector (40) laterally away from the longitudinal axis (LA) of shaft assembly (30) at a desired angle (a). In the present example, articulation is controlled through an articulation control knob (35) which is located at the proximal end of shaft assembly (30). Closure ring (36) and end effector (40) pivot about an axis that is perpendicular to the longitudinal axis (LA) of shaft assembly (30) in response to rotation of knob (35). Articulation section (34) is configured to communicate longitudinal translation of closure tube (32) to closure ring (36), regardless of whether articulation section (34) is in a straight configuration or an articulated configuration. By way of example only, articulation section (34) and/or articulation control knob (35) may be constructed and operable in accordance with at least some of the teachings of U.S. Pub. No. 2014/0243801, entitled "Surgical Instrument End Effector Articulation Drive with Pinion and Opposing Racks," published Aug. 28, 2014, issued as U.S. Pat. No. 9,186,142 on Nov. 17, 2015, the disclosure of which is incorporated by reference herein; and/or U.S. Pub. No. 2015/0374360, entitled "Articulation Drive Features for Surgical Stapler," published Dec. 31, 2015, issued as U.S. Pat. No. 10,292,701 on May 21, 2019 the disclosure of which is incorporated by reference herein; and/or in accordance with the various teachings below. Other suitable forms that articulation section (34) and articulation knob (35) may take will be apparent to those of ordinary skill in the art in view of the teachings herein.

As shown in FIG. 1, shaft assembly (30) of the present example further includes a rotation knob (31). Rotation knob (31) is operable to rotate the entire shaft assembly (30) and end effector (40) relative to handle assembly (20) about the longitudinal axis (LA) of shaft assembly (30). Of course, shaft assembly (30) may have a variety of other components, features, and operabilities, in addition to or in lieu of any of those noted above. By way of example only, at least part of shaft assembly (30) is constructed in accordance with at least some of the teachings of U.S. Pub. No. 2014/0239038, entitled "Surgical Instrument with Multi-Diameter Shaft," published Aug. 28, 2014, issued as U.S. Pat. No. 9,795,379 on Oct. 24, 2017, the disclosure of which is incorporated by reference herein. Other suitable configurations for shaft assembly (30) will be apparent to those of ordinary skill in the art in view of the teachings herein.

B. Exemplary End Effector

Figure 3:
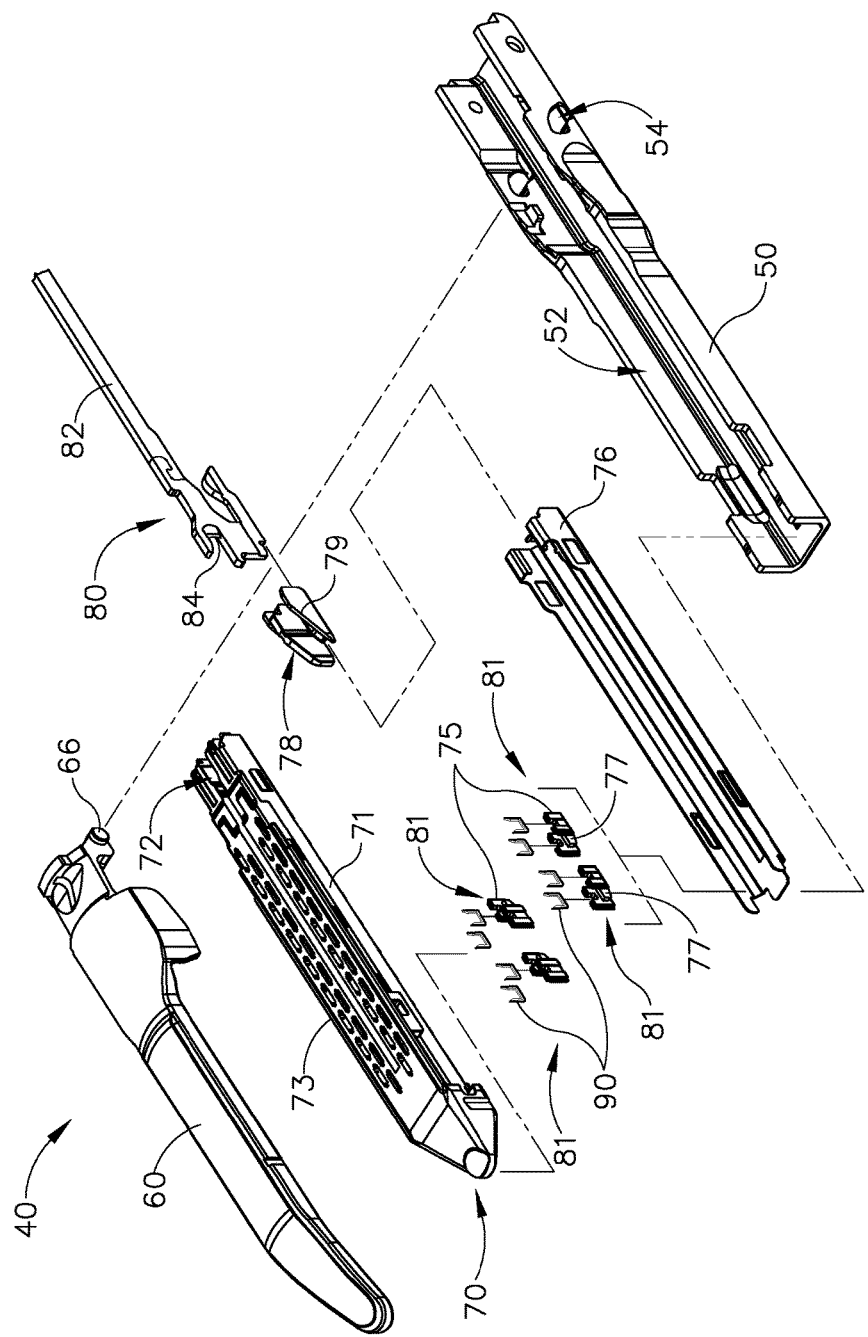
FIG. 3 depicts an exploded perspective view of the end effector and staple cartridge of FIG. 2.

As also shown in FIGS. 1-3, end effector (40) of the present example includes a lower jaw (50) and a pivotable anvil (60). Anvil (60) includes a pair of integral, outwardly extending pins (66) that are disposed in corresponding curved slots (54) of lower jaw (50). Anvil (60) is pivotable toward and away from lower jaw (50) between an open position (shown in FIG. 2) and a closed position (shown in FIG. 1). Use of the term "pivotable" (and similar terms with "pivot" as a base) should not be read as necessarily requiring pivotal movement about a fixed axis. For instance, in the present example, anvil (60) pivots about an axis that is defined by pins (66), which slide along curved slots (54) of lower jaw (50) as anvil (60) moves toward lower jaw (50). In such versions, the pivot axis translates along the path defined by slots (54) while anvil (60) simultaneously pivots about that axis. In addition or in the alternative, the pivot axis may slide along slots (54) first, with anvil (60) then pivoting about the pivot axis after the pivot axis has slid a certain distance along the slots (54). It should be understood that such sliding/translating pivotal movement is encompassed within terms such as "pivot," "pivots," "pivotal," "pivotable," "pivoting," and the like. Of course, some versions may provide pivotal movement of anvil (60) about an axis that remains fixed and does not translate within a slot or channel, etc.

As best seen in FIG. 3, lower jaw (50) of the present example defines a channel (52) that is configured to receive a first exemplary staple cartridge (70). Staple cartridge (70) may be inserted into channel (52), end effector (40) may be actuated, and then staple cartridge (70) may be removed and replaced with another staple cartridge (70). Lower jaw (50) thus releasably retains staple cartridge (70) in alignment with anvil (60) for actuation of end effector (40). In some versions, lower jaw (50) is constructed in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that lower jaw (50) may take will be apparent to those of ordinary skill in the art in view of the teachings herein.

As best seen in FIGS. 2-3, staple cartridge (70) of the present example comprises a cartridge body (71) and a tray (76) secured to the underside of cartridge body (71). The upper side of cartridge body (71) presents a deck (73), against which tissue may be compressed when anvil (60) is in a closed position. Cartridge body (71) further defines a longitudinally extending channel (72) and a plurality of staple pockets (74). A staple (90) is positioned in each staple pocket (74). A staple driver (75) is also positioned in each staple pocket (74), underneath a corresponding staple (90), and above tray (76). As will be described in greater detail below, staple drivers (75) are operable to translate upwardly in staple pockets (74) to thereby drive staples (90) upwardly through staple pockets (74) and into engagement with anvil (60). Staple drivers (75) are driven upwardly by a wedge sled (78), which is captured between cartridge body (71) and tray (76), and which translates longitudinally through cartridge body (71).

In one example, a pair of staple drivers (75) are connected together by a driver cam (77) extending therebetween to form a driver assembly (81). Wedge sled (78) includes a pair of obliquely angled cam surfaces (79), which are configured to engage driver cam (77) and thereby simultaneously drive the connected pair of staple drivers (75) upwardly as wedge sled (78) translates longitudinally through cartridge (70). For instance, when wedge sled (78) is in a proximal position, staple drivers (75) are in downward positions and staples (90) are located in staple pockets (74). As wedge sled (78) is driven to the distal position by a translating knife member (80), wedge sled (78) drives staple drivers (75) upwardly, thereby driving staples (90) out of staple pockets (74) and into staple forming pockets (64) that are formed in the underside (65) of anvil (60). Thus, staple drivers (75) translate along a vertical dimension as wedge sled (78) translates along a horizontal dimension.

In some versions, staple cartridge (70) is constructed and operable in accordance with at least some of the teachings of U. U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016, the disclosure of which is incorporated by reference herein. In addition or in the alternative, staple cartridge (70) may be constructed and operable in accordance with at least some of the teachings of U.S. Pub. No. 2014/0239044, entitled "Installation Features for Surgical Instrument End Effector Cartridge," published Aug. 28, 2014, issued as U.S. Pat. No. 9,808,248 on Nov. 7, 2017, the disclosure of which is incorporated by reference herein. Other suitable forms that staple cartridge (70) may take will be apparent to those of ordinary skill in the art in view of the teachings herein.

As best seen in FIG. 2, anvil (60) of the present example comprises a longitudinally extending channel (62) and a plurality of staple forming pockets (64). Channel (62) is configured to align with channel (72) of staple cartridge (70) when anvil (60) is in a closed position. Each staple forming pocket (64) is positioned to lie over a corresponding staple pocket (74) of staple cartridge (70) when anvil (60) is in a closed position. Staple forming pockets (64) are configured to deform the legs of staples (90) when staples (90) are driven through tissue and into anvil (60). In particular, staple forming pockets (64) are configured to bend the legs of staples (90) to secure the formed staples (90) in the tissue. Anvil (60) may be constructed in accordance with at least some of the teachings of U.S. Pub. No. 2014/0239042, entitled "Integrated Tissue Positioning and Jaw Alignment Features for Surgical Stapler," published Aug. 28, 2014, issued as U.S. Pat. No. 9,517,065 on Dec. 13, 2016; at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017; and/or at least some of the teachings of U.S. Pub. No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (60) may take will be apparent to those of ordinary skill in the art in view of the teachings herein.

In the present example, knife member (80) is configured to translate through end effector (40). As best seen in FIG. 3, knife member (80) is secured to the distal end of a firing beam (82), which extends through a portion of shaft assembly (30). As best seen in FIG. 2, knife member (80) is positioned in respective channels (62, 72) of anvil (60) and staple cartridge (70). Knife member (80) includes a distally presented cutting edge (84) that is configured to sever tissue that is compressed between anvil (60) and deck (73) of staple cartridge (70) as knife member (80) translates distally through end effector (40). As noted above, knife member (80) also drives wedge sled (78) distally as knife member (80) translates distally through end effector (40), thereby driving staples (90) through tissue and against anvil (60) into formation.

C. Exemplary Actuation of End Effector

In the present example, anvil (60) is driven toward lower jaw (50) by advancing closure ring (36) distally relative to end effector (40). Closure ring (36) cooperates with anvil (60) through a camming action to drive anvil (60) toward lower jaw (50) in response to distal translation of closure ring (36) relative to end effector (40). Similarly, closure ring (36) may cooperate with anvil (60) to open anvil (60) away from lower jaw (50) in response to proximal translation of closure ring (36) relative to end effector (40). By way of example only, closure ring (36) and anvil (60) may interact in accordance with at least some of the teachings of U.S. Pub. No. 2014/0239036, entitled "Jaw Closure Feature for End Effector of Surgical Instrument," published Aug. 28, 2014, issued as U.S. Pat. No. 9,839,421 on Dec. 12, 2017, the disclosure of which is incorporated by reference herein; and/or in accordance with at least some of the teachings of U.S. Pub. No. 2015/0374361, entitled "Jaw Opening Feature for Surgical Stapler," published Dec. 31, 2015, the disclosure of which is incorporated by reference herein.

As noted above, handle assembly (20) includes pistol grip (22) and closure trigger (24). As also noted above, anvil (60) is closed toward lower jaw (50) in response to distal advancement of closure ring (36) from an open configuration to a closed configuration with lower jaw (50). In the present example, closure trigger (24) is pivotable toward pistol grip (22) to drive closure tube (32) and closure ring (36) distally. Various suitable components that may be used to convert pivotal movement of closure trigger (24) toward pistol grip (22) into distal translation of closure tube (32) and closure ring (36) relative to handle assembly (20) will be apparent to those of ordinary skill in the art in view of the teachings herein.

Also in the present example, surgical instrument (10) provides motorized control of firing beam (82). In particular, surgical instrument (10) includes motorized components that are configured to drive firing beam (82) distally in response to pivoting of firing trigger (26) toward pistol grip (22). In some versions, a motor (not shown) is contained in pistol grip (22) and receives power from battery pack (28). This motor is coupled with a transmission assembly (not shown) that converts rotary motion of a drive shaft of the motor into linear translation of firing beam (82). By way of example only, the features that are operable to provide motorized actuation of firing beam (82) may be configured and operable in accordance with at least some of the teachings of U.S. Pat. No. 8,210,411, entitled "Motor-Driven Surgical Instrument," issued Jul. 3, 2012, the disclosure of which is incorporated by reference herein.; U.S. Pat. No. 8,453,914, entitled "Motor-Driven Surgical Cutting Instrument with Electric Actuator Directional Control Assembly," issued Jun. 4, 2013, the disclosure of which is incorporated by reference herein; and/or U.S. Pub. No. 2015/0272575, entitled "Surgical Instrument Comprising a Sensor System," published Oct. 1, 2015, issued as U.S. Pat. No. 9,913,642 on Mar. 13, 2018, the disclosure of which is incorporated by reference herein.

It should also be understood that any other components or features of surgical instrument (10) may be configured and operable in accordance with any of the various references cited herein. Additional exemplary modifications that may be provided for surgical instrument (10) will be described in greater detail below. Various suitable ways in which the below teachings may be incorporated into surgical instrument (10) will be apparent to those of ordinary skill in the art. Similarly, various suitable ways in which the below teachings may be combined with various teachings of the references cited herein will be apparent to those of ordinary skill in the art. It should therefore be understood that the teachings below may be readily incorporated into the various surgical instruments taught in the various references that are cited herein. It should also be understood that the below teachings are not limited to surgical instrument (10) or devices taught in the references cited herein. The below teachings may be readily applied to various other kinds of surgical instruments, including instruments that would not be classified as surgical staplers. Various other suitable devices and settings in which the below teachings may be applied will be apparent to those of ordinary skill in the art in view of the teachings herein.

II. Exemplary Surgical Stapler with Hydraulic Actuation System

In some instances, it may be desirable to equip end effector (40) with a hydraulic system to provide selective movement of deck (73) and staples (90) for receiving tissue and forming staples (90) within the tissue captured between anvil (60) and deck (73). Such a hydraulic system may enable deck (73) to conform to various types of tissue thicknesses and densities while providing equivalent drive forces to each staple (90) simultaneously. For example, some tissues may have varying density and/or thickness due to various anatomical structures present within the tissue. Using a conventional stapler to capture the tissue and drive staples (90) as discussed above may result in relatively high and/or unequal pressure being applied across such tissue. Enlarging a gap between anvil (60) and deck (73) may enable a modified version of end effector (40) to receive thicker and/or denser portions of tissue therebetween with less pressure applied to the tissue. A modified version of deck (73) may also conform to the tissue to accommodate the relatively thinner or less dense portion of tissue.

Furthermore, another hydraulic system operatively engaged with staples (90) may provide a reactionary force back on the fluid within the hydraulic system at each staple (90). The fluid may thus simultaneously act on each staple (90), directly or indirectly, with an equivalent driving force while also accommodating various deck positions. One such example of a staple cartridge (110) with a hydraulic actuation system (112) (see FIG. 13) having a hydraulic deck system (114) (see FIG. 13) and a hydraulic staple drive system (116) (see FIG. 13) is shown and described below in greater detail. It will be appreciated that alternative hydraulic systems and decks may be used alone or in combination for deploying staples (90). Staple cartridge (110) may be configured to replace staple cartridge (70) described above for use with surgical instrument (10). Alternatively, another surgical instrument, such as a surgical instrument (118) described below, may be configured to accommodate one or more features of staple cartridge (110).

Figure 4:
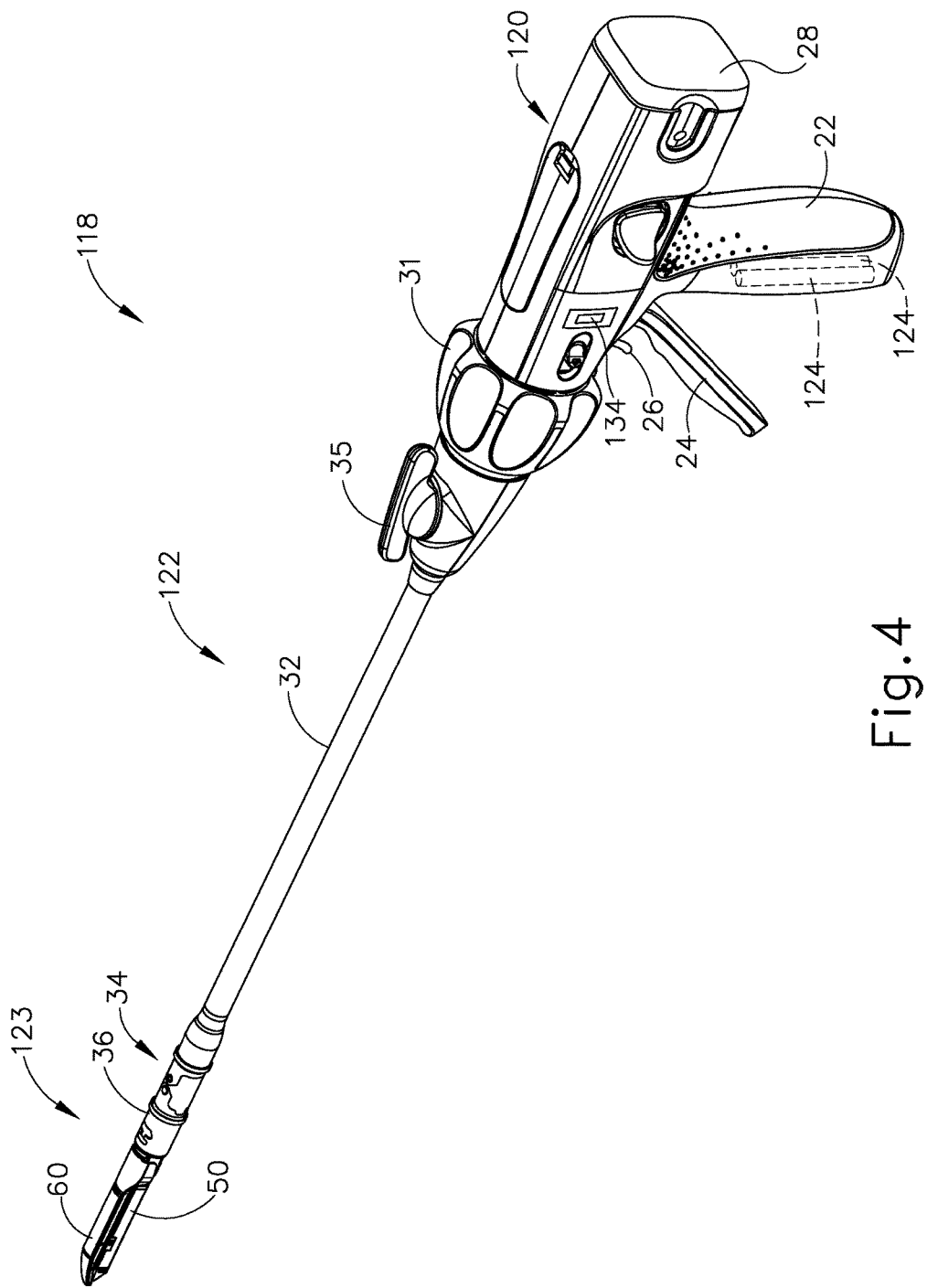
FIG. 4 depicts a perspective view of another exemplary articulating surgical stapling instrument.
Figure 5:
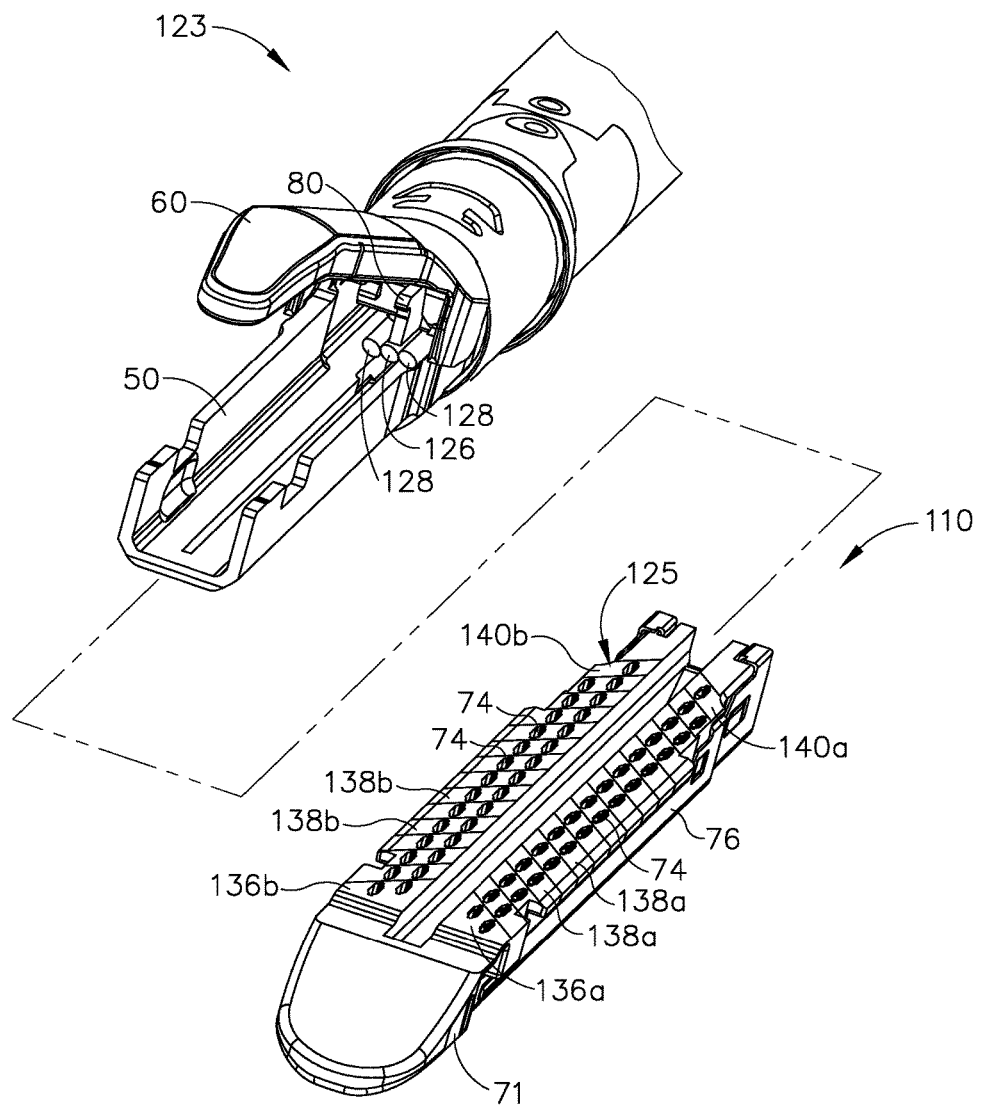
FIG. 5 depicts a partially exploded perspective view of an end effector of the instrument of FIG. 4, with the end effector in an open configuration and a second exemplary staple cartridge.
Figure 6:
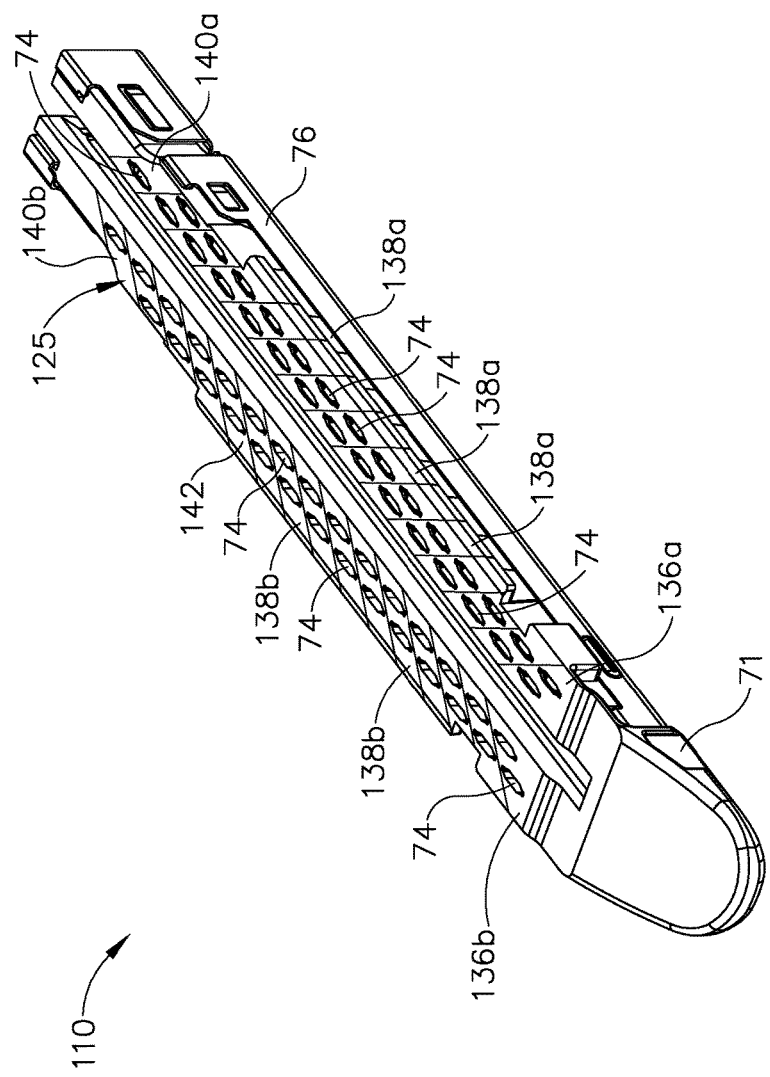
FIG. 6 depicts a perspective view of the staple cartridge of FIG. 5.
Figure 9:
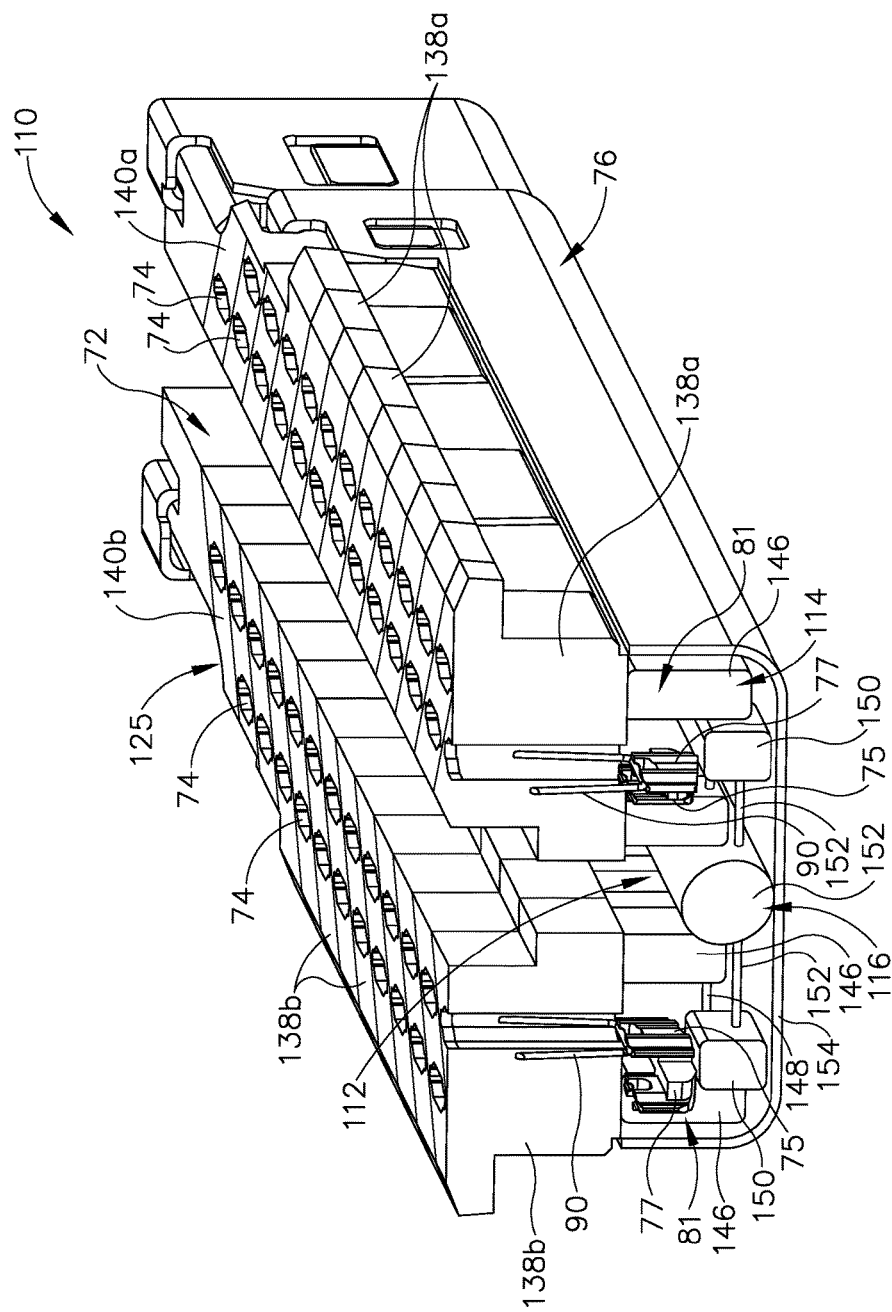
FIG. 9 depicts a perspective cross-sectional view of the staple cartridge of FIG. 5, taken along line 9-9 of FIG. 8.
Figure 10:
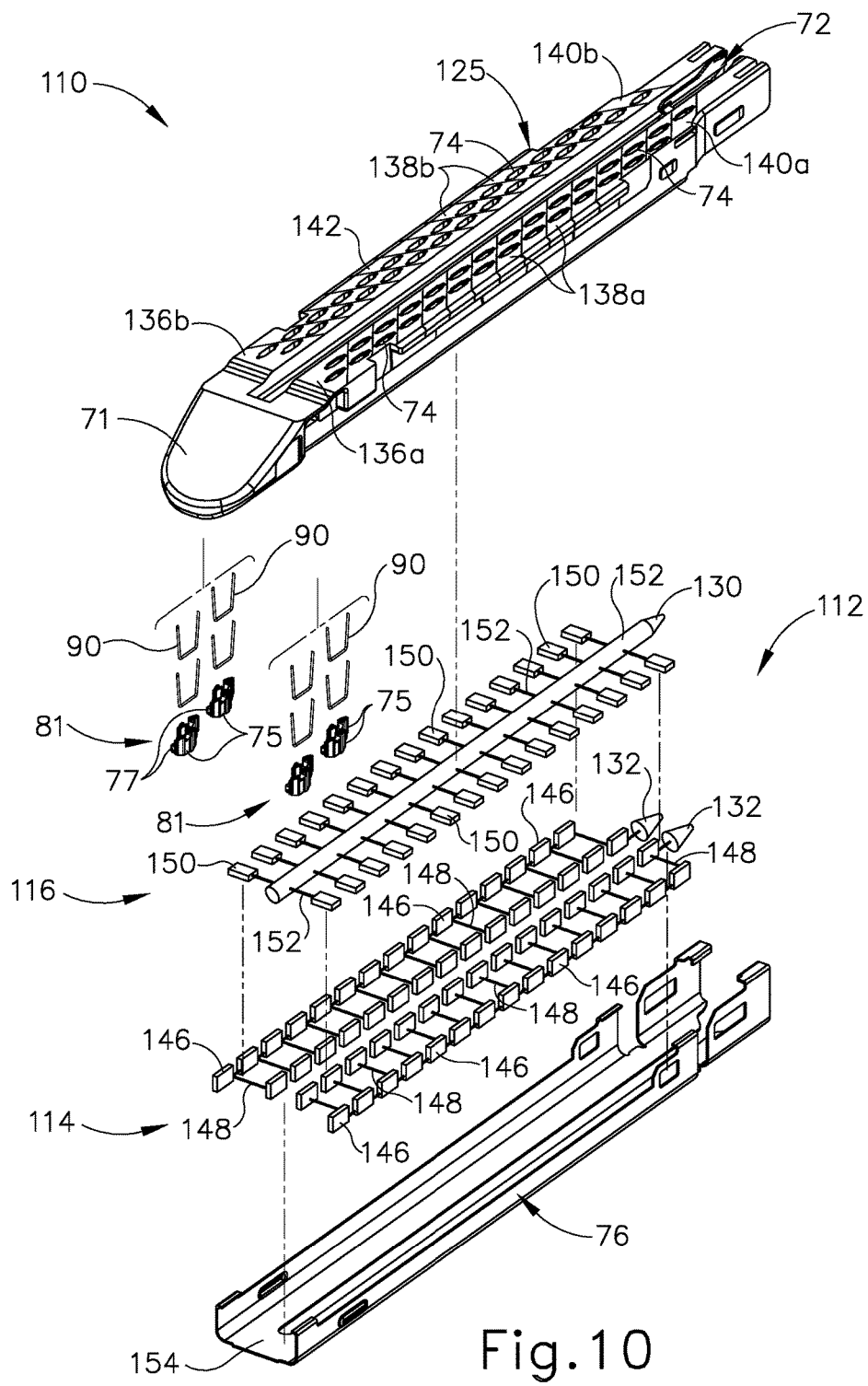
FIG. 10 depicts an exploded perspective view of the staple cartridge of FIG. 5, showing a hydraulic actuation system including a hydraulic deck system and a hydraulic staple drive system.
Figure 11:
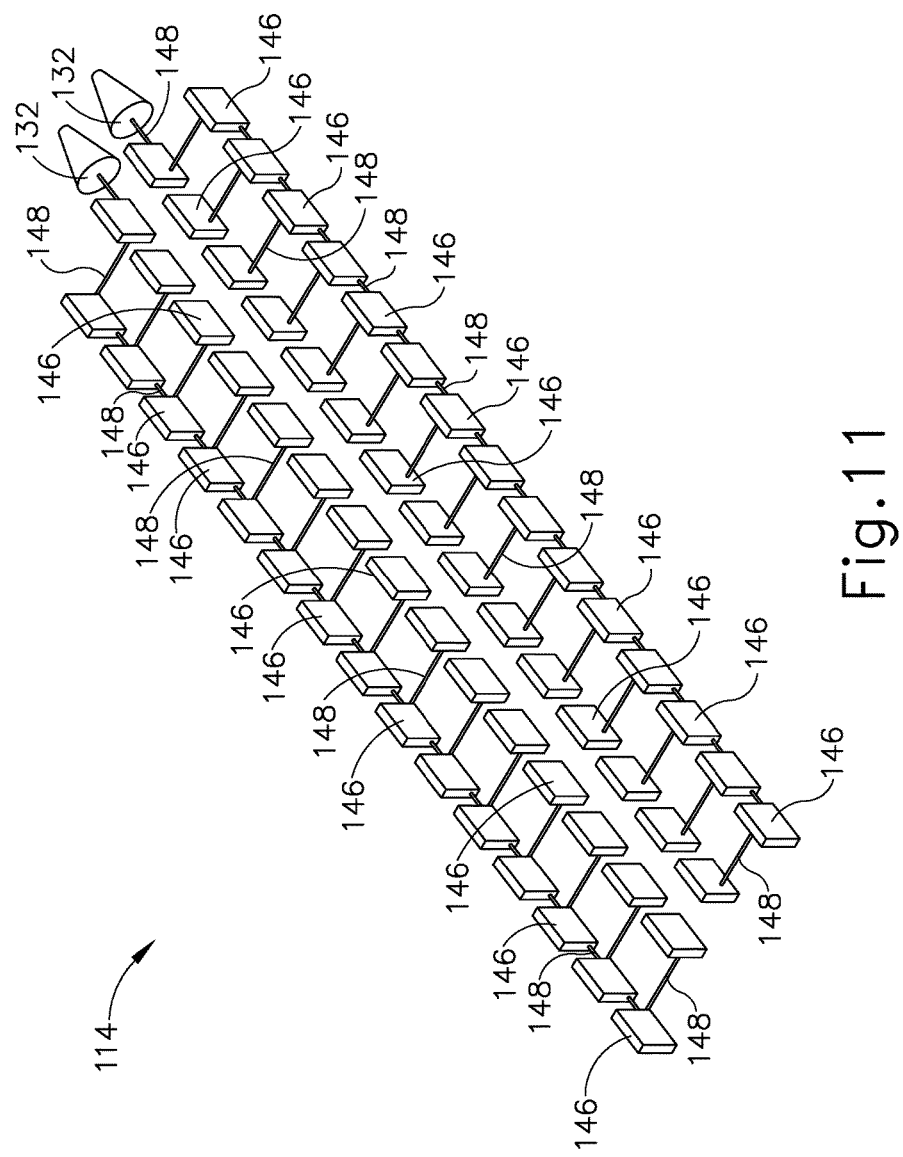
FIG. 11 depicts a perspective view of the hydraulic deck system of FIG. 10.
Figure 12:
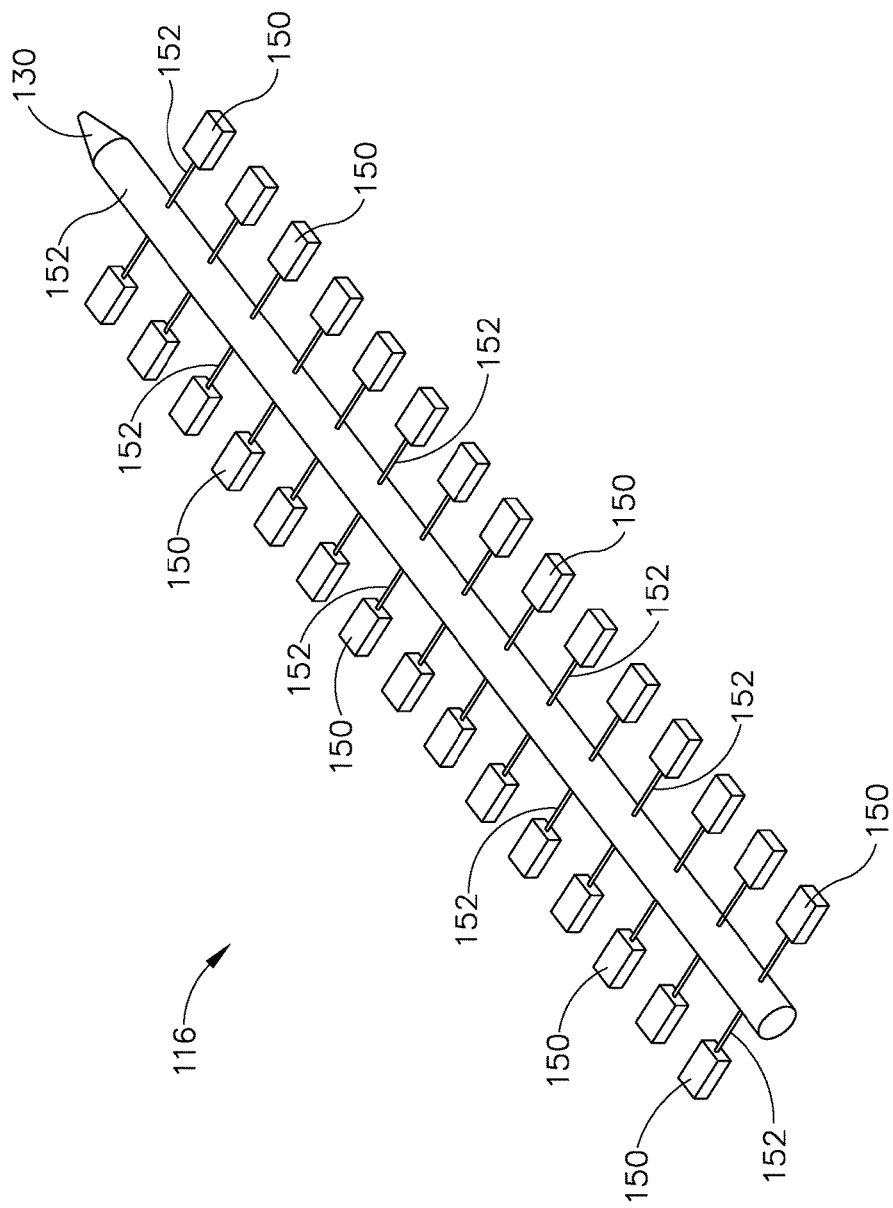
FIG. 12 depicts a perspective view of the hydraulic staple drive system of FIG. 10.

A. Exemplary Hydraulic Staple Cartridge with a Hydraulic Actuation System and Adjustable Deck FIG. 4-5 show another exemplary surgical stapling and severing instrument (118) that includes a handle assembly (120), a shaft assembly (122), and an end effector (123). As discussed above with respect to end effector (40) (see FIG. 1), end effector (123) and a distal portion of shaft assembly (122) are sized for insertion, in a nonarticulated state as depicted in FIG. 4, through a trocar cannula to a surgical site in a patient for performing a surgical procedure. Alternatively, end effector (123) and a distal portion of shaft assembly (122) may be inserted through a thoracotomy or via some other route to a surgical site. Surgical instrument (118) shares various similarities with surgical instrument (10) (see FIG. 1) with like numbers indicating like features described above in greater detail. In addition, end effector (123) includes staple cartridge (110) having hydraulic actuation system (112) (see FIG. 13) fluidly connected to at least one fluid supply, such as a pair of fluid supply cartridges (124). Hydraulic actuation system (112) (see FIG. 13) includes hydraulic deck system (114) (see FIG. 13) and hydraulic staple drive system (116) (see FIG. 13) for respectively adjusting a height of an adjustable deck (125) and driving a plurality of staples (90) toward anvil (60). Hydraulic deck system (114) (see FIG. 13) thus distributes clamping pressure between anvil (60) and deck (125) across tissue relatively evenly, while hydraulic staple drive system (116) (see FIG. 13) accommodates movement of deck (125) to reduce the likelihood of damaging tissue during use.

Staple cartridge (110) removably secures to end effector (123) such that lower jaw (50) receives tray (76). Staple cartridge (110) also fluidly connects to a drive fluid supply conduit (126) and a pair of deck fluid supply conduits (128) positioned on each lateral side of drive fluid supply conduit (126). Drive and deck fluid supply conduits (126, 128) extend proximally from a proximal end portion of lower jaw (50), through shaft assembly (30), and into handle assembly (120) to fluidly connect with fluid supply cartridges (124) contained with handle assembly (120). In the present example, each deck fluid supply conduit (128) fluidly connects to one of fluid supply cartridges (124), and drive fluid supply conduit (126) fluid connects to the other one of fluid supply cartridges (124). Alternatively, drive and deck fluid supply conduits (126, 128) may collectively fluidly connect to one or more fluid supply cartridges (124). The fluid in fluid supply conduits (128) is more particularly a liquid in the present example. However, it will be appreciated that any fluid configured to operate hydraulic actuation system (112) (see FIG. 13) may be used. In the event that handle assembly (120) is reusable, fluid supply cartridges (124) may be refilled or replaced for use as desirable. While staple cartridge (110) receives the fluid from fluid supply cartridges (224) positioned exterior of staple cartridge (110) itself, one or more fluid supplies, such as fluid supply cartridges (124), may be alternatively contained within staple cartridge (110) for storing fluid within staple cartridge (110). Fluid supplies are those not intended to be unnecessarily limited to fluid supply cartridges (124) as described herein.

As shown in FIG. 4 and FIGS. 6-8, hydraulic staple drive system (116) has a drive fluid port (130), and hydraulic deck system (114) has a pair of deck fluid ports (132). Each of drive and deck fluid ports (130, 132) extends proximally from the proximal end portion of staple cartridge (110) with the pair of deck fluid ports (132) positioned on each lateral side of drive fluid port (130). Drive and deck fluid ports (130, 132) are thus positioned to be received by and fluidly seal against drive and deck fluid supply conduits (126, 128) for receiving fluid from fluid supply cartridges (124). To this end, firing trigger (26) is operatively connected to fluid supply cartridges (124) and configured to direct fluid from fluid supply cartridges (124), through drive fluid supply conduit (126), and into hydraulic staple drive system (116) for driving staples (90) as discussed above. In contrast, handle assembly (120) has a deck set switch (134) operatively connected to fluid supply cartridges (124) and configured to direct fluid from fluid supply cartridges (124), through deck fluid supply conduits (126), and into hydraulic deck system (116) for adjusting the height of deck (125) as discussed below in additional detail. Deck set switch (134) and trigger (26) are configured to be manipulated independently of each other by the user such that the height of deck (125) is set independently of deploying staples (90).

In the example shown and described herein, directing the fluid into staple cartridge (110) causes deck (125) to translate upwardly from tray (76) toward an upper position, whereas removing the fluid from staple cartridge (110) causes deck (125) to translate downwardly toward a lower position. Deck (125) includes a plurality of deck pieces (136a, 136b, 138a, 138b, 140a, 140b) that collectively define an upper surface (142) of deck (125), which is configured to conform to tissue positioned thereagainst. More particularly, distal deck pieces (136a, 136b) and proximal deck pieces (140a, 140b) are configured to respectively bound the distal and proximal end portions of upper surface (142), whereas intermediate deck pieces (138a, 138b) are side-by-side therebetween. Deck pieces (136a, 138a, 140a) arranged on one lateral side of channel (72) are respectively mirror images of deck pieces (136b, 138b, 140b) on the other lateral side of channel (72). While some spacing may be provided between deck pieces (136a, 136b, 138*a*, 138*b*, 140*a*, 140*b*), deck pieces (136*a*, 136*b*, 138*a*, 138*b*, 140*a*, 140*b*) generally provide a continuous upper surface (142) for receiving tissue thereagainst. Deck pieces (136*a*, 136*b*, 138*a*, 138*b*, 140*a*, 140*b*) are nevertheless movable relative to each other.

Deck (125) further includes staple pockets (74) configured to respectively contain the plurality of staples (90) for storage and deployment during use. Deck (125) of the present example has two offset staple pockets (74) in each of distal and intermediate deck pieces (136*a*, 136*b*, 138*a*, 138*b*), whereas proximal deck pieces (140*a*, 14*b*) have one staple pocket (74) each. Thus, staple pockets (74) and staples (90) received therein are arranged in a pair of rows on one lateral side of channel (72) and another pair of rows on another lateral side of channel (72). However, it will be appreciated that deck (125) may include any arrangement of deck pieces (136*a*, 136*b*, 138*a*, 138*b*) to accommodate any desirable arrangement of staple pockets (74) and staples (90). While deck (125) generally translates between the upper and lower positions as a collection of deck pieces (136*a*, 136*b*, 138*a*, 138*b*, 140*a*, 140*b*), each deck piece (136*a*, 136*b*, 138*a*, 138*b*, 140*a*, 140*b*) is configured to translate, to at least some extent, independent of the other deck pieces (136*a*, 136*b*, 138*a*, 138*b*, 140*a*, 140*b*) in the present example. Movement of deck pieces (136*a*, 136*b*, 138*a*, 138*b*, 140*a*, 140*b*) relative to each other for conforming to the tissue will be discussed below in additional detail.

Hydraulic actuation system (112) of staple cartridge (110) is shown in FIGS. 9-13 in detail. With respect to FIGS. 9-11, hydraulic deck system (114) and hydraulic staple drive system (116) generally nest together between tray (76) and deck (125) to reduce the overall footprint of hydraulic deck system (114) for containment within tray (76). Hydraulic deck system (114) includes a plurality of deck expanders (146) fluidly connected to each other and deck fluid port (132) via a plurality of deck fluid coupling conduits (148). Similarly, hydraulic staple drive system (116) includes a plurality of staple expanders (150) fluidly connected to each other and drive fluid port (130) via a plurality of drive fluid coupling conduits (152). Thus, each of deck and staple expanders (146, 150) is configured to receive the fluid to expand from a contracted state to an expanded state for respectively increasing the height of deck (125) and deploying staples (90). In addition, deck expander (146) is configured to have the fluid withdrawn therefrom for respectively decreasing the height of deck (125). The term "expander" is therefore not intended to be limited to only expansion but also include contraction from a relatively expanded state. In some versions, each deck and staple expander (146, 150) is in the form of a balloon and may be also referred to herein as deck and staple balloons (146, 150). While hydraulic deck and staple expanders (146, 150) are in the form of deck and staple balloons (146, 150) as shown and described herein, hydraulic deck and staple expanders (146, 150) may alternatively comprise another expansion member or an expansion assembly, such as a hydraulic piston, configured to elongate in at least one dimension for engaging driver assemblies (81) and/or deck pieces (136*a*, 136*b*, 138*a*, 138*b*, 140*a*, 140*b*). Thus, the term "expander" is not intended to be limited to exemplary deck and staple balloons (146, 150).

Hydraulic deck system (114) includes deck (125) and deck balloons (146) discussed above. More particularly, deck balloons (146) are arranged in two rows on each lateral side of channel (72). An outer row of deck balloons (146) is positioned longitudinally distal of an inner row of deck balloons (146) such that each deck piece (136*a*, 136*b*, 138*a*, 138*b*, 140*a*, 140*b*) is cooperatively supported by one deck balloon (146) of the outer row and one deck balloon (146) of the inner row. The inner and outer rows of deck balloons (146) thereby support opposing lateral end portions for each deck piece (136*a*, 136*b*, 138*a*, 138*b*, 140*a*, 140*b*) directly above a floor (154) of tray (76).

Lower portions of deck pieces (136*a*, 136*b*, 138*a*, 138*b*, 140*a*, 140*b*) are configured to translate within tray (76), whereas upper surface (142) remains above tray (76). In the contracted state, deck balloons (146) support deck pieces (136*a*, 136*b*, 138*a*, 138*b*, 140*a*, 140*b*) with a relatively small height such that deck (125) is closer to floor (154) of tray (76). In the expanded state, deck balloons (146) support deck pieces (136*a*, 136*b*, 138*a*, 138*b*, 140*a*, 140*b*) with a relatively large height such that deck (125) is farther from floor (154) of tray (76). Deck pieces (136*a*, 136*b*, 138*a*, 138*b*, 140*a*, 140*b*) are generally positioned at equivalent heights relative to each other without the application of additional forces applied to one or more portions of deck (125). However, in the event that unequal forces are applied along deck (125), the fluid will disperse throughout hydraulic deck system (114) to dissipate pressure equally across deck pieces (136*a*, 136*b*, 138*a*, 138*b*, 140*a*, 140*b*). In turn, some deck balloons (146) may contract while other deck balloons (146) expand to move deck pieces (136*a*, 136*b*, 138*a*, 138*b*, 140*a*, 140*b*) relative to each other to conform deck (125) to tissue received thereagainst (e.g., see FIG. 14C).

As shown in FIGS. 9-10 and FIGS. 12-13, staple balloons (150) are positioned respectively between each driver assembly (81) and floor (154) of tray (76) such that driver assemblies (81) respectively straddle staple balloons (150). More particularly, each driver cam (77) of driver assembly (81) is supported directly on respective staple balloons (150). As staple balloons (150) move from the contracted state toward the expanded state, each balloon (150) respectively engages each driver assembly (81) to force each staple driver (75) and staple (90) resting thereon upwardly toward anvil (60) (see FIG. 5). Furthermore, each staple balloon (150) is sized and configured to fit below its respective deck piece (136*a*, 136*b*, 138*a*, 138*b*, 140*a*, 140*b*) so as not to interfere with movement of deck (125) regardless of the expansion state of either the plurality of deck balloons (146) or the plurality of staple balloons (150). In other words, in addition to hydraulic deck system (114) being fluidly isolated from hydraulic staple drive system (116) for independent operation, hydraulic deck system (114) is also mechanically isolated from hydraulic staple driver system (116) so that each hydraulic system (112, 116) operates independently of the other hydraulic system (112, 116).

Figure 13:
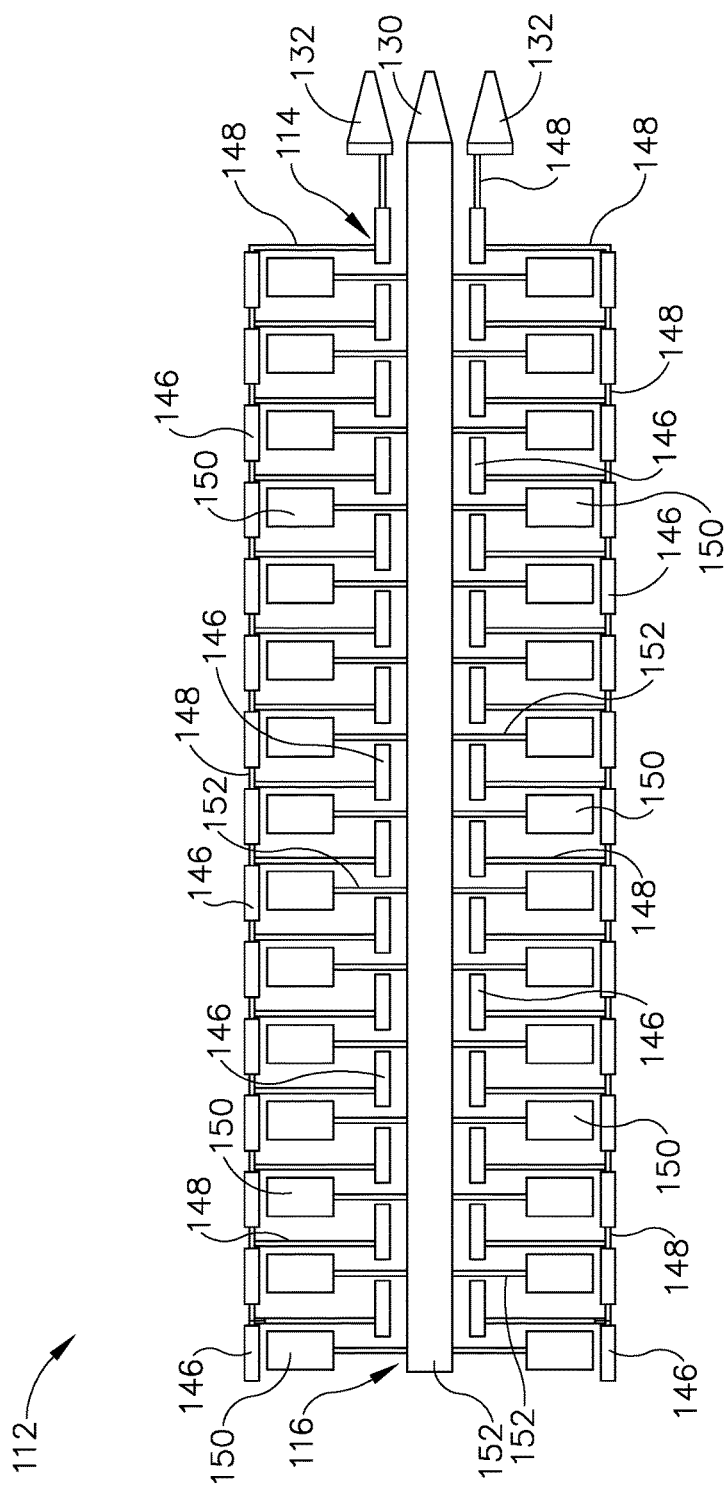
FIG. 13 depicts a top plan view of the hydraulic actuation system of FIG. 10.

FIG. 13 more clearly shows one central row of staple balloons (150) arranged on each side of channel (72) (see FIG. 9) and the inner and outer rows of deck balloons (146) positioned on each lateral side of the central row of staple balloons (150). In the present example, one staple balloon (150) is positioned between a pair of inner and outer deck balloons (146) below each respective deck piece (136*a*, 136*b*, 138*a*, 138*b*, 140*a*, 140*b*) for deploying staples (90) and adjusting deck height. However, deck and staple balloons (146, 150) may be positioned in any arrangement for engagement with portions of deck (125) and driver assemblies (81). Furthermore, any desirable number of deck and staple balloons (146, 150) may be used for adjusting deck height and deploying staples (90). The invention described herein is thus not intended to be unnecessarily limited to the particular arrangement or number of deck and staple balloons shown and described herein.

B. Exemplary Actuation of End Effector including a Hydraulic Actuation System

As shown in FIG. 4 and FIGS. 14A-14B, the user may selectively manipulate deck set switch (134) to adjust deck (125) to any desirable position, such as the upper position of FIG. 14A, the lower position of FIG. 14B, or any other position therebetween. The height of deck (125) is generally discussed with respect to the height from lower jaw (50) to upper surface (142) of deck (125). However, adjustment of deck height is configured to similarly adjust a depth of a gap (156) between anvil (60) and upper surface (142) for receiving tissues of various densities and thicknesses to avoid damaging tissue when capturing the tissue with end effector (123) in the closed configuration. For example, relatively thick tissue may be overly compressed with a conventional deck in the upper position, so the user may adjust deck (125) toward the lower position to increase the depth of gap (156) to accommodate the relatively thick tissue with less compression.

FIG. 14C shows one exemplary portion of tissue (158) having various densities. The user accordingly adjusted the height of deck (125) to avoid overly compressing and damaging tissue (158); and captured tissue (158) between anvil (60) and upper surface (142) of deck (125). Furthermore, the reaction force of tissue (158) on deck pieces (136a, 136b, 138a, 138b, 140a, 140b) and deck balloons (146) dissipated the fluid throughout hydraulic deck system (114) to equalize fluid pressure throughout. In turn, deck balloons (146) support deck pieces (136a, 136b, 138a, 138b, 140a, 140b) at a variety of heights to conform to tissue (158) and apply equivalent pressure along deck (125). In the present example, deck pieces (136a, 136b, 138a, 138b, 140a, 140b) are connected to adjacent deck pieces (136a, 136b, 138a, 138b, 140a, 140b) via resilient linkages (160). Resilient linkages (160) are generally configured to mechanically secure deck pieces (136a, 136b, 138a, 138b, 140a, 140b) together as an assembly of deck (125) and resiliently return deck to a generally flat upper surface (125) when tissue (158) is not received thereagainst.

Figure 15D:
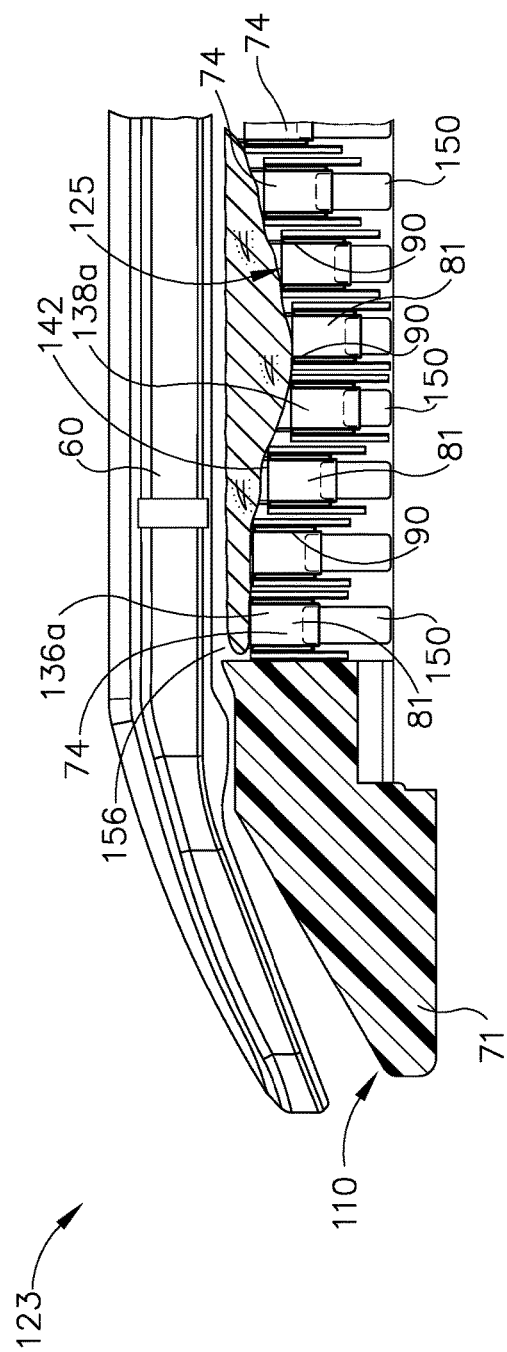
FIG. 15D depicts an enlarged cross-sectional view of the distal end of the end effector of FIG. 5 taken along section line 15A-15A of FIG. 8, with the hydraulic staple drive system in a fired state.

As shown in FIGS. 15A-15B, hydraulic staple drive system (116) and staples (90) generally remain unmoved during adjustment of deck (125) as discussed above. Once tissue (158) is captured in the closed configuration of anvil (60) and lower jaw (50), the user may then pull trigger (26) to deploy staples (90) as shown in FIGS. 15C-15D. To this end, with drivers (75) and staples (90) being supported on fluidly connected staple balloons (150), each driver (75) is directed upwardly with equivalent expansion force since pressure from reaction forces of drivers (75) will distribute evenly throughout the fluid. Thus, regardless of the amount of upward travel of driver assemblies (81), each staple (90) will puncture tissue (158) and form within tissue (158) with equivalent force. Expansion forces on drivers (75) will continue to increase until the expansion force of staple balloons (150) sufficiently forms staples (90) within tissue (158) and fluidly seals tissue (132) as knife member (80) cuts tissue (132).

While hydraulic actuation system (112) of the present example is configured to avoid damaging tissue by distributing compression forces relatively equally along the tissue, hydraulic actuation system (112) may further be configured to limit a pressure applied to the tissue to a predetermined maximum pressure. For example, one or both of hydraulic deck system (114) and hydraulic staple drive system (116) may include a pressure relief feature, such as a valve, to limit the maximum fluid pressure within systems (112, 114). Alternatively, hydraulic activation system (112) may be configured to actively monitor fluid pressure to cease providing fluid to portions of staple cartridge (110) to limit pressure to the predetermined maximum pressure. Other suitable variations will be apparent to those of ordinary skill in the art in view of the teachings herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument, comprising: (a) a body; (b) a shaft assembly extending distally from the body; and (c) an end effector extending distally from the shaft assembly, wherein the end effector includes: (i) a first jaw having an anvil, wherein the anvil is configured to form a plurality of staples received thereagainst, (ii) a second jaw, wherein the first jaw is movable relative to the second jaw from an open configuration toward a closed configuration for capturing the tissue therebetween and forming the staples therein, and (iii) a staple cartridge, wherein the staple cartridge includes: (A) the plurality of staples, (B) a body, wherein the body is received by the second jaw, and (C) a deck having a plurality of staple pockets such that the plurality of staples are configured to pass through staple pockets, wherein the deck is configured to selectively move relative to the body from a first position to a second position for adjusting a height of the deck relative to the anvil while the body is received in the second jaw.

EXAMPLE 2

The surgical instrument of Example 1, wherein the staple cartridge further includes a hydraulic deck expander, wherein the hydraulic deck expander is configured to receive a fluid and thereby expand from a contracted state toward an expanded state, and wherein the hydraulic deck expander is configured to engage the deck and selectively move the deck from the first position to the second position upon expanding to the expanded state.

EXAMPLE 3

The surgical instrument of Example 2, wherein the staple cartridge further includes a tray received within the second jaw, and wherein the hydraulic expander is positioned between the tray and the deck to support the deck relative to the tray.

EXAMPLE 4

The surgical instrument of any one or more of Examples 2 through 3, wherein at least one of the handle assembly and the shaft assembly further includes a fluid supply fluidly connected to the hydraulic deck expander and containing a fluid for selectively expanding the hydraulic deck expander.

EXAMPLE 5

The surgical instrument of Example 4, wherein the handle assembly further includes a deck set switch operatively connected to the fluid supply and configured to selectively adjust the height of the deck relative to the anvil via the fluid.

EXAMPLE 6

The surgical instrument of any one or more of Examples 1 through 5, wherein the deck is translatably mounted relative to the second jaw.

EXAMPLE 7

The surgical instrument of Example 6, wherein the first position is a low deck position, the second position is a high deck position, and wherein the low deck position of the deck is closer to the second jaw than the high deck position.

EXAMPLE 8

The surgical instrument of of any one or more of Examples 1 through 7, wherein the staple cartridge further includes a hydraulic staple expander configured to receive a fluid, wherein the hydraulic staple expander is configured to selectively expand from a contracted state toward an expanded state upon receiving the fluid, and wherein the hydraulic staple expander is configured to direct at least one of the plurality of staples toward the anvil for forcing the at least one of the plurality of staples against the anvil and forming the at least one of the plurality of staples within the tissue.

EXAMPLE 9

The surgical instrument of Example 8, wherein the hydraulic staple expander is operable to expand independently of the selective movement of the deck, and wherein the deck is configured to move independently of the selective expansion of the hydraulic staple expander.

EXAMPLE 10

The surgical instrument of Example 9, wherein the staple cartridge further includes a hydraulic deck expander, wherein the hydraulic deck expander is configured to receive a fluid and thereby expand from a contracted state toward an expanded state, and wherein the hydraulic deck expander is configured to engage the deck and selectively move the deck from the first position to the second position upon expanding to the expanded state.

EXAMPLE 11

The surgical instrument of Example 10, wherein the hydraulic deck expander comprises a deck balloon, wherein the hydraulic staple expander comprises a staple balloon.

EXAMPLE 12

The surgical instrument of of any one or more of Examples 1 through 11, wherein the deck is defined by a plurality of deck pieces, and wherein each of the deck pieces is movable relative to a remainder of the deck pieces such that the deck is configured to conform to tissue received thereagainst.

EXAMPLE 13

The surgical instrument of Example 12, wherein the staple cartridge further includes a plurality of hydraulic deck expanders, wherein each of the plurality of hydraulic deck expanders is configured to receive a fluid and thereby expand from a contracted state toward an expanded state, and wherein the plurality of hydraulic deck expanders is configured to engage the deck and selectively move the deck from the first position to the second position upon expanding to the expanded state.

EXAMPLE 14

The surgical instrument of Example 13, wherein each of the plurality of deck pieces is supported by a pair of the plurality of hydraulic deck expanders.

EXAMPLE 15

The surgical instrument of Example 14, wherein the staple cartridge further includes a plurality of hydraulic staple expanders configured to receive the fluid, wherein each of the hydraulic staple expanders is configured to selectively expand from a contracted state toward an expanded state upon receiving the fluid, wherein each of the hydraulic staple expanders is configured to direct at least one of the plurality of staples toward the anvil for forcing the at least one of the plurality of staples against the anvil and forming the at least one of the plurality of staples within the tissue, and wherein each of the hydraulic staple expanders is positioned between the pair of the plurality of hydraulic deck expanders.

EXAMPLE 16

A staple cartridge for a surgical instrument, comprising: (a) a tray configured to be received by the surgical instrument; (b) a plurality of staples; and (c) a deck offset from the tray and having a plurality of staple pockets such that the plurality of staples are respectively positioned within the plurality of staple pockets, wherein the deck is movably mounted relative to the tray and is configured to selectively move from a first position to a second position for adjusting a height of the deck relative to the tray.

EXAMPLE 17

The staple cartridge of Example 16, further comprising a hydraulic deck expander positioned between the tray and the deck, wherein the hydraulic deck expander is configured to receive a fluid and thereby expand from a contracted state toward an expanded state, and wherein the hydraulic deck expander is configured to engage the deck and selectively move the deck from the first position to the second position upon expanding to the expanded state.

EXAMPLE 18

The staple cartridge of Example 17, further comprising a fluid port fluidly connected to the hydraulic deck expander, wherein the fluid port is configured to fluidly connect to the surgical instrument for receiving the fluid therefrom and expanding the hydraulic deck expander.

Example 19

The staple cartridge of any one or more of Examples 16 through 18, wherein the deck is defined by a plurality of deck pieces, and wherein each of the deck pieces is movable relative to a remainder of the deck pieces such that the deck is configured to conform to the tissue received thereagainst.

Example 20

A method of stapling tissue with a surgical instrument having a staple cartridge, wherein the staple cartridge includes: (a) a tray configured to be received by the surgical instrument; (b) a plurality of staples; and (c) a deck offset from the tray and having a plurality of staple pockets such that the plurality of staples are respectively positioned within the plurality of staple pockets, wherein the deck is movably mounted relative to the tray and configured to selectively move from a first position to a second position for adjusting a height of the deck relative to the tray; the method comprising: (a) adjusting the height of the deck from the first position to the second position; (b) receiving tissue against the deck; and (c) actuating the staple cartridge to drive the staples through the tissue.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued April 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 2, 2015, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012 issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; and/or U.S. Pub. No. 2012/0205421, entitled "Robotically- Controlled Surgical End Effector System with Rotary Actuated Closure Systems," published Aug. 16, 2012, issued as U.S. Pat. No. 8,573,465 on Nov. 2, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body;
   (b) a shaft assembly extending distally from the body; and
   (c) an end effector extending distally from the shaft assembly, wherein the end effector includes:
      (i) a first jaw having an anvil, wherein the anvil is configured to form a plurality of staples received thereagainst,
      (ii) a second jaw, wherein the first jaw is movable relative to the second jaw from an open configuration toward a closed configuration for capturing a tissue therebetween and forming the staples therein, and
      (iii) a staple cartridge, wherein the staple cartridge includes:
         (A) the plurality of staples,
         (B) a cartridge body, wherein the cartridge body is received by the second jaw,
         (C) a deck defined by at least a first deck piece and a second deck piece having a plurality of staple pockets such that the plurality of staples are configured to pass through staple pockets, wherein the first and second deck pieces are movable relative to each other such that the deck is configured to conform to the tissue compressed thereagainst,
         (D) a deck support system operatively connected to the first and second deck pieces and configured to selectively move each of the first and second deck pieces relative to at least a portion of the cartridge body from a first position to a second position for adjusting a height of the deck relative to the anvil while the cartridge body is received in the second jaw, and
         wherein the deck support system is configured to independently move the first and second deck pieces respectively to a first adjustable deck height and a different, second adjustable deck height upon compression while conforming to the tissue, and
         wherein the deck support system is further configured to support the first and second deck pieces when compressed against the tissue at the differing first and second adjustable deck heights for equalizing compression along the tissue.

2. The surgical instrument of claim 1, wherein the deck support system includes a first hydraulic deck expander and a second hydraulic deck expander, wherein the first and second hydraulic deck expanders are configured to receive a deck system fluid and thereby respectively expand from a first deck contracted state toward a first deck expanded state and a second deck contracted state toward a second deck expanded state, and wherein the first and second hydraulic deck expanders are configured to engage the first and second deck pieces and selectively move the first and second deck pieces upon expanding to the first and second deck expanded states.

3. The surgical instrument of claim 2, wherein the staple cartridge further includes a tray received within the second jaw, and wherein the first and second hydraulic expanders are positioned between the tray and the deck to support the deck relative to the tray.

4. The surgical instrument of claim 2, wherein at least one of the body and the shaft assembly further includes a fluid supply fluidly connected to the first and second hydraulic deck expanders and containing the deck system fluid for selectively expanding the first and second hydraulic deck expanders.

5. The surgical instrument of claim 4, wherein the body further includes a deck set switch operatively connected to the fluid supply and configured to selectively adjust the height of the deck relative to the anvil via the deck system fluid.

6. The surgical instrument of claim 2, wherein the first deck piece is supported by a pair of the first hydraulic deck expanders, and wherein the second deck piece is supported by a pair of the second hydraulic deck expanders.

7. The surgical instrument of claim 6, wherein the staple cartridge further includes a first hydraulic staple expander and a second hydraulic staple expander configured to receive a staple system fluid, wherein the first and second hydraulic staple expanders is configured to selectively and respectively expand from a first staple contracted state toward a first staple expanded state and a second staple contracted state toward a second staple expanded state upon receiving the staple system fluid, wherein each of the first and second hydraulic staple expanders is configured to direct at least one of the plurality of staples toward the anvil for forcing the at least one of the plurality of staples against the anvil and forming the at least one of the plurality of staples within the tissue, wherein the first hydraulic staple expander is positioned between the pair of first hydraulic deck expanders, and wherein the second hydraulic staple expander is positioned between the pair of second hydraulic deck expanders.

8. The surgical instrument of claim 1, wherein the deck is translatably mounted relative to the second jaw.

9. The surgical instrument of claim 8, wherein the first position is a low deck position, the second position is a high deck position, and wherein the low deck position of the deck is closer to the second jaw than the high deck position.

10. The surgical instrument of claim 1, wherein the plurality of staples includes a first staple and a second staple, wherein the staple cartridge further includes a staple drive system operatively connected to the first and second staples and is configured to independently move the first and second staples respectively to a first adjustable staple height and a different, second adjustable staple height against the anvil for accommodating the tissue, wherein the staple drive system is further configured to drive the first and second staples with equal force when driven through the tissue and against the anvil at differing first and second adjustable staple heights for equalizing compression along the tissue.

11. The surgical instrument of claim 10, wherein the staple drive system further includes a first hydraulic staple expander and a second hydraulic staple expander configured to receive a staple system fluid, wherein the first and second hydraulic staple expanders are respectively configured to selectively expand from a first staple contracted state toward a first staple expanded state and a second staple contracted state toward a second staple expanded state upon receiving the staple system fluid, and wherein the first and second hydraulic staple expanders are configured to respectively direct the first and second staples toward the anvil for forcing the first and second staples against the anvil and forming the first and second staples within the tissue.

12. The surgical instrument of claim 11, wherein the first and second hydraulic staple expanders are operable to expand independently of the selective movement of the deck, and wherein the deck is configured to move independently of the selective expansion of the first and second hydraulic staple expanders.

13. The surgical instrument of claim 12, wherein the deck support system includes a first hydraulic deck expander and a second hydraulic deck expander, wherein the first and second hydraulic deck expanders are configured to receive a deck system fluid and thereby respectively expand from a first deck contracted state toward a first deck expanded state and a second deck contracted state toward a second deck expanded state, and wherein the first and second hydraulic deck expanders are configured to engage the first and second deck pieces and selectively move the first and second deck pieces upon expanding to the first and second deck expanded states.

14. The surgical instrument of claim 13, wherein the first and second hydraulic deck expanders respectively comprise a first deck balloon and a second deck balloon, and wherein the first and second hydraulic staple expanders respectively comprise a first staple balloon and a second staple balloon.

15. A staple cartridge for a surgical instrument, comprising:
(a) a tray configured to be received by the surgical instrument;
(b) a plurality of staples;
(c) a deck offset from the tray and having a plurality of staple pockets such that the plurality of staples are respectively positioned within the plurality of staple pockets, wherein the deck is defined by a first deck piece and a second deck piece that are movable relative to each other and the tray such that the deck is configured to conform to a tissue compressed thereagainst; and
(d) a deck support system operatively connected to the first and second deck pieces and configured to independently move the first and second deck pieces respectively to a first adjustable deck height and a different, second adjustable deck height upon compression while conforming to the tissue, and
wherein the deck support system is further configured to support the first and second deck pieces when compressed against the tissue at the differing first and second adjustable deck heights for equalizing compression along the tissue.

16. The staple cartridge of claim 15, wherein the deck support system further includes a first hydraulic deck expander and a second hydraulic deck expander positioned between the tray and the deck, wherein the first and second hydraulic deck expanders are configured to receive a fluid and thereby expand from a contracted state toward an expanded state, and wherein the first and second hydraulic deck expanders are respectively configured to engage the first and second deck pieces and selectively move the first and second deck pieces to the respective first and second adjustable deck heights.

17. The staple cartridge of claim 16, further comprising a fluid port fluidly connected to the hydraulic deck expanders, wherein the fluid port is configured to fluidly connect to the surgical instrument for receiving the fluid therefrom and expanding the hydraulic deck expanders.

18. The staple cartridge of claim 15, wherein the plurality of staples includes a first staple and a second staple, wherein the staple cartridge further comprises a staple drive system operatively connected to the first and second staples and is configured to independently move the first and second staples respectively to a first adjustable staple height and a different, second adjustable staple height against the anvil for accommodating the tissue, wherein the staple drive system is further configured to drive the first and second staples with equal force when driven through the tissue and against the anvil at differing first and second adjustable staple heights for equalizing compression along the tissue.

19. A method of stapling a tissue with a surgical instrument having a staple cartridge, wherein the staple cartridge includes:
(a) a tray configured to be received by the surgical instrument;
(b) a plurality of staples; and
(c) a deck offset from the tray and having a plurality of staple pockets such that the plurality of staples are respectively positioned within the plurality of staple pockets, wherein the deck is movably mounted relative to the tray and configured to selectively move from a first position to a second position for adjusting a height of the deck relative to the tray;
the method comprising:
(a) adjusting the height of the deck of the staple cartridge relative to the tray of the staple cartridge from the first position to the second position;
(b) compressing the tissue against a first deck piece of the deck with a first pressure and a second deck piece of the deck with a second pressure;

(c) adjusting the height of the first deck piece relative to the second deck piece thereby conforming the first and second deck pieces to the tissue and equalizing the first and second pressures of the first and second deck pieces against the tissue; and
(d) actuating the staple cartridge to drive the plurality of staples of the staple cartridge respectively from the plurality of staple pockets and through the tissue.

20. The method of claim 19, further comprising limiting pressure applied to the tissue by the first and second deck pieces to a predetermined maximum pressure.

* * * * *